(12) United States Patent
Li et al.

(10) Patent No.: US 8,232,271 B2
(45) Date of Patent: Jul. 31, 2012

(54) HETEROCYCLIC ANTIVIRAL COMPOUNDS

(75) Inventors: Jim Li, San Francisco, CA (US); Alfred Sui-Ting Lui, Sunnyvale, CA (US); Kristen Lynn McCaleb, Daly City, CA (US); Francisco Xavier Talamas, Mountain View, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 277 days.

(21) Appl. No.: 12/609,160

(22) Filed: Oct. 30, 2009

(65) Prior Publication Data
US 2010/0111900 A1    May 6, 2010

Related U.S. Application Data

(60) Provisional application No. 61/197,943, filed on Oct. 30, 2008.

(51) Int. Cl.
*C07D 401/02* (2006.01)
*C07D 213/62* (2006.01)
*A61K 31/44* (2006.01)

(52) U.S. Cl. ......... 514/222.2; 514/227.8; 514/235.5; 514/253.13; 514/318; 514/335; 514/336; 544/7; 544/59; 544/131; 544/360; 546/193; 546/255; 546/268.1; 546/300

(58) Field of Classification Search .............. None
See application file for complete search history.

(56) References Cited

U.S. PATENT DOCUMENTS
2006/0040927 A1    2/2006    Blake et al.

FOREIGN PATENT DOCUMENTS
| WO | WO00/09543 A2 | 2/2000 |
| WO | WO01/85172 A1 | 11/2001 |
| WO | WO2009/039135 A1 | 3/2009 |
| WO | 2009099929 A1 | 8/2009 |
| WO | 2010/010017 A1 | 1/2010 |
| WO | WO2010/111436 A2 | 9/2010 |
| WO | WO2010/111437 A1 | 9/2010 |

OTHER PUBLICATIONS
European Patent Office Communication dated Feb. 23, 2012.

*Primary Examiner* — Zinna Northington Davis
(74) *Attorney, Agent, or Firm* — Brian L. Buckwalter

(57) ABSTRACT

Compounds having the formula I wherein $R^1$, $R^2$, $R^{3a}$, $R^{3b}$, $R^{3c}$, $R^4$, $R^5$ and p are as defined herein are Hepatitis C virus NS5b polymerase inhibitors. Also disclosed are compositions and methods for treating an HCV infection and inhibiting HCV replication.

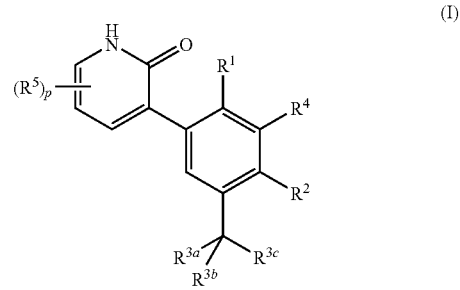

(I)

11 Claims, No Drawings

HETEROCYCLIC ANTIVIRAL COMPOUNDS

CROSS REFERENCE TO PRIOR APPLICATIONS

This application claims the benefit of priority to U.S. Ser. No. 61/197,943 filed Oct. 30, 2008 which is hereby incorporated by reference in their entirety.

FIELD OF THE INVENTION

The present invention provides non-nucleoside compounds of formula I, and certain derivatives thereof, which are inhibitors of RNA-dependent RNA viral polymerase. These compounds are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND

Hepatitis C virus is the leading cause of chronic liver disease throughout the world. (Boyer, N. et al., *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., *Flaviviridae:* The viruses and their replication. In: Fields Virology, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a highly conserved 5' untranslated region (UTR), a long open reading frame encoding a polyprotein precursor of approximately 3011 amino acids, and a short 3' UTR.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forms and J. Bukh, *Clinics in Liver Disease* 1999 3:693-716; J. Bukh et al., *Semin. Liv. Dis.* 1995 15:41-63). Unfortunately Type 1 infectious is more resistant to therapy than either type 2 or 3 genotypes (N. N. Zein, *Clin. Microbiol. Rev.*, 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of non-structural protein 5) remain unknown. It is believed that most of the non-structural proteins encoded by the HCV RNA genome are involved in RNA replication Currently a limited number of approved therapies are available for the treatment of HCV infection. New and existing therapeutic approaches for treating HCV infection and inhibiting of HCV NS5B polymerase activity have been reviewed: R. G. Gish, *Sem. Liver. Dis.*, 1999 19:5; Di Besceglie, A. M. and Bacon, B. R., *Scientific American*, October: 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patent on experimental therapy for hepatitis C virus infection (1999-2002), *Exp. Opin. Ther. Patents* 2003 13(11):1707-1723; M. P. Walker et al., Promising Candidates for the treatment of chronic hepatitis C, *Exp. Opin. Investing. Drugs* 2003 12(8): 1269-1280; S.-L. Tan et al., Hepatitis C Therapeutics: Current Status and Emerging Strategies, *Nature Rev. Drug Discov.* 2002 1:867-881; J. Z. Wu and Z. Hong, Targeting NS5B RNA-Dependent RNA Polymerase for Anti-HCV Chemotherapy, *Curr. Drug Targ.-Infect. Dis.* 2003 3(3):207-219.

Ribavirin (1-((2R,3R,4S,5R)-3,4-Dihydroxy-5-hydroxymethyl-tetrahydro-furan-2-yl)-1H-[1,2,4]triazole-3-carboxylic acid amide; Virazole®) is a synthetic, non-interferon-inducing, broad-spectrum antiviral nucleoside analog. Ribavirin has in vitro activity against several DNA and RNA viruses including Flaviviridae (Gary L. Davis. *Gastroenterology* 2000 118:S104-S114). Although, in monotherapy ribavirin reduces serum amino transferase levels to normal in 40% of patients, it does not lower serum levels of HCV-RNA. Ribavirin also exhibits significant toxicity and is known to induce anemia. Viramidine is a ribavirin prodrug converted ribavirin by adenosine deaminase to in hepatocytes. (J. Z. Wu, *Antivir. Chem. Chemother.* 2006 17(1):33-9)

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon beta, type 2 includes interferon gamma. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon −2a and a 40 kD branched mono-methoxy PEG and PEG-INTRON® is a conjugate of interferon −2b and a 12 kD mono-methoxy PEG. (B. A. Luxon et al., *Clin. Therap.* 2002 24(9):13631383; A. Kozlowski and J. M. Harris, *J. Control. Release* 2001 72:217-224).

Combination therapy of HCV with ribavirin and interferon-α currently is the optimal therapy for HCV. Combining ribavirin and PEG-IFN (infra) results in a sustained viral response (SVR) in 54-56% of patients with type 1 HCV. The SVR approaches 80% for type 2 and 3 HCV. (Walker, supra) Unfortunately, combination therapy also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the NS3 protease, the NS3 helicase and the NS5B polymerase. The RNA-dependent RNA polymerase is absolutely essential for replication of the single-stranded, positive sense, RNA genome. This enzyme has elicited significant interest among medicinal chemists.

Nucleoside inhibitors can act either as a chain terminator or as a competitive inhibitor that interferes with nucleotide binding to the polymerase. To function as a chain terminator the nucleoside analog must be taken up by the cell in vivo and be converted in vivo to its triphosphate form to compete as a substrate at the polymerase nucleotide binding site. This conversion to the triphosphate is commonly mediated by cellular kinases which impart additional structural limitations on any nucleoside. In addition this requirement for phosphorylation limits the direct evaluation of nucleosides as inhibitors of HCV replication to cell-based assays (J. A. Martin et al., U.S. Pat. No. 6,846,810; C. Pierra et al., *J. Med. Chem.* 2006 49(22):6614-6620; J. W. Tomassini et al., *Antimicrob. Agents and Chemother.* 2005 49(5):2050; J. L. Clark et al., *J. Med. Chem.* 2005 48(17):2005).

SUMMARY OF THE INVENTION

There is currently no preventive treatment of Hepatitis C virus (HCV) and currently approved therapies, which exist only against HCV, are limited. Design and development of new pharmaceutical compounds is essential.

The present invention provides a compound according to formula I, or a pharmaceutically acceptable salt thereof, wherein:

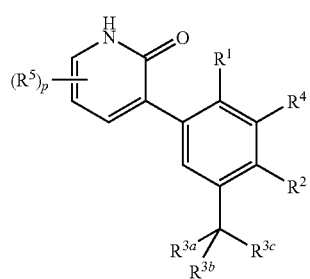

(I)

$R^1$ is (alkylene)$_{0-6}$COX, (alkylene)$_{0-6}$NR$^a$R$^b$, (alkylene)$_{0-6}$CN, $C_{1-6}$ hydroxyalkyl, or $C_{1-3}$ alkylsulfonyl-(alkylene)$_{0-3}$;

X is hydrogen, hydroxy, $C_{1-6}$ alkoxy or NR$^c$R$^d$;

$R^2$ is hydrogen, $C_{1-6}$ alkoxy, $C_{1-3}$ alkyl or halogen;

$R^a$ is (a) hydrogen, (b) $C_{1-6}$ alkyl, (c) $C_{1-6}$ acyl, (d) aroyl, (e) —SO$_2$—$C_{1-6}$ alkyl, (f) —SO$_2$-aryl, (g) —SO$_2$—$C_{1-3}$ arylalkyl, (h) aryl-$C_{1-3}$ alkyl, or (i) SO$_2$NR$^e$R$^f$ wherein R$^e$ and R$^f$ are independently hydrogen or $C_{1-3}$ alkyl, (j) pyridinoyl, (k) $C_{3-7}$ cycloalkyl-carbonyl or (l) CONHR$^e$R$^f$, (m) —SO$_2$—$C_{3-6}$ cycloalkyl or (n) 4-methanesulfonylamino-pyrrolidine-2-carbonyl wherein said cycloalkane moiety is substituted by $C_{1-3}$ alkylsulfonylamino and wherein said aryl, said aroyl and said pyridinoyl are each independently optionally substituted with one to three groups independently selected from hydroxy, $C_{1-6}$ alkoxy, $C_{1-6}$ alkoxy, amino, $C_{1-3}$ alkylamino, $C_{1-3}$ dialkylamino, $C_{1-6}$ acylamino, $C_{1-6}$ alkylsulfonylamino, bis-($C_{1-6}$ alkylsulfonyl)amino, $C_{1-6}$ alkyl and halogen;

$R^b$ is hydrogen $C_{1-6}$ alkyl, optionally substituted aryl, $C_{1-6}$ hydroxyalkyl, $C_{1-3}$ acyloxy-$C_{1-6}$ alkyl, heterocyclyl-$C_{1-3}$ alkyl; $C_{3-6}$ cycloalkyl-$C_{1-3}$ alkyl, pyrrolidin-3-ylmethyl, 1-acetyl-pyrrolidin-3-ylmethyl, piperidin-4-yl, or pyridinyl; or, $R^a$ and $R^b$ together are C(=O)C(Me)$_2$NHC(=O), (CH$_2$)$_{3-5}$S(=O)$_2$, (CH$_2$)$_{2-5}$C(=O), C(=O)CH$_2$C(Me)$_2$CH$_2$C(=O), HC=CC(Br)=CHC(=O), C(=O)(CH$_2$)$_{2-4}$C(=O), HC=CC(=O)CEt$_2$(=O) or S(=O)$_2$NR$^6$(CH$_2$)$_{3-5}$ wherein R$^6$ is hydrogen, $C_{1-6}$ alkyl or Boc; or, $R^a$ and $R^b$ together with the nitrogen to which they are attached are (a) phthaloyl (b) 1-methyl-1,3-dihydro-2-oxo-benzoimidazol-3-yl, (c) 5-oxo-pyrrolidin-1-yl optionally substituted by $C_{1-6}$ carboalkoxy, carboxyl or $C_{1-3}$ hydroxymethyl, (d) 3-hydroxymethyl-pyrrolidin-1-yl, (e) 2-oxo-oxazolidin-3-yl optionally substituted with $C_{1-6}$ alkyl or (f) 3-oxo-2,3-dihydro-1H-isoindolyl optionally substituted with $C_{1-6}$ alkylsulfonylamino or $C_{3-6}$ cycloalkylsulfonylamino;

$R^c$ is hydrogen, $C_{1-6}$ alkyl;

$R^d$ is hydrogen, $C_{1-6}$ alkyl; pyridinyl-$C_{1-3}$ alkyl, cyano-$C_{1-3}$ alkyl, 4-$C_{1-3}$ alkoxy-$C_{1-6}$ alkyl or aryl-$C_{1-3}$ alkyl optionally substituted with halogen; or, $R^c$ and $R^d$ together are (CH$_2$)$_2$X$^1$(CH$_2$)$_2$ wherein X$^1$ is O, SO$_2$ or NR$^7$ wherein R$^7$ is hydrogen, $C_{1-6}$ alkyl, $C_{1-3}$ alkoxy-$C_{1-3}$ alkyl or $C_{1-3}$ acyl; or, $R^c$ and $R^d$ together with the nitrogen to which they are attached are 4,4-difluoro-piperidin-1-yl, 4-phenoxy-piperidin-1-yl, 3-hydroxy-azetidine, 4-cyano-piperidin-1-yl, 3-(hydroxylmethyl)pyrrolidin-1-yl or 2-hydroxymethyl-morpholin-4-yl;

$R^{3a}$, $R^{3b}$ and $R^{3c}$ (i) when taken independently are selected independently from $C_{1-3}$ alkyl, $C_{1-2}$ alkoxy or $C_{1-2}$ fluoroalkyl or (ii) when taken together, $R^{3a}$ and $R^{3b}$ together are $C_{2-4}$ methylene and $R^{3c}$ is $C_{1-3}$ alkyl;

$R^4$ is hydrogen, $C_{1-6}$ alkyl;

$R^5$ is hydrogen, halogen or $C_{1-3}$ alkyl; or, p is zero to three; or, a pharmaceutically acceptable salt thereof.

The present invention also provides a method for treating a disease caused by the Hepatitis C Virus (HCV) virus by administering a therapeutically effective quantity of a compound according to formula I to a patient in need thereof. The compound can be administered alone or co-administered with other antiviral compounds or immunomodulators.

The present invention also provides a method for inhibiting replication of HCV in a cell by administering a compound according to formula I in an amount effective to inhibit HCV.

The present invention also provides a pharmaceutical composition comprising a compound according to formula I and at least one pharmaceutically acceptable carrier, diluent or excipient.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or " ------ " drawn through a bond each refer to the point of attachment of a functional group or other chemical moiety to the rest of the molecule of which it is a part. Thus, for example:
$MeC(=O)OR^4$ wherein

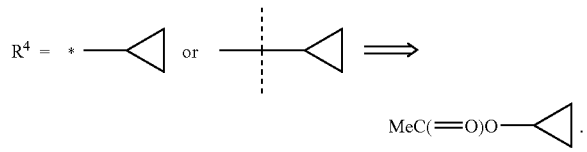

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

It will be appreciated by the skilled artisan that some of the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the skilled artisan that substitution of the tropane ring can be in either endo- or exo-configuration, and the present invention covers both configurations. The present invention includes all the individual stereoisomers (e.g. enantiomers), racemic mixtures or partially resolved mixtures of the compounds of formulae I and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, .alpha.-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively the racemates can be covalently linked to a chiral compound (auxillary) to produce diastereomers which can be separated by chromatography or by fractional crystallization after which time the chiral auxiliary is chemically removed to afford the pure enantiomers.

The compounds of formula I contain at least one basic center and suitable acid addition salts are formed from acids which form non-toxic salts. Examples of salts of inorganic acids include the hydrochloride, hydrobromide, hydroiodide, chloride, bromide, iodide, sulphate, bisulphate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulphate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.,* 1977 66:1-19 and G. S. Paulekuhn et al. *J. Med. Chem.* 2007 50:6665.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as *Fieser and Fieser's Reagents for Organic Synthesis*; Wiley & Sons: New York, Volumes 1-21; R. C. LaRock, *Comprehensive Organic Transformations,* 2nd edition Wiley-VCH, New York 1999; *Comprehensive Organic Synthesis,* B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry* II, A. R. Katritzky and C. W. Rees (Eds) Pergamon, Oxford 1996, vol. 1-11; and *Organic Reactions,* Wiley & Sons: New York, 1991, Volumes 1-40 and will be familiar to those skilled in the art.

In on embodiment of the present invention there is provided a compound according to formula I wherein $R^1$, $R^2$, $R^{3a}$, $R^{3b}$, $R^{3c}$, $R^4$, $R^5$, $R^6$, $R^a$, $R^b$, $R^c$, $R^d$, $R^e$, $R^f$, X, $X^1$, n and p are as defined herein above. The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

In a second embodiment of the present invention there is provided a compound according to formula I wherein $R^2$ is hydrogen or $C_{1-6}$ alkoxy and $R^{3a}$, $R^{3b}$ and $R^{3c}$ are methyl.

In a third embodiment of the present invention there is provided a compound according to formula I wherein $R^1$ is (alkylene)$_{0-6}$NR$^a$R$^b$, $R^a$ is optionally substituted aroyl, $C_{3-7}$ cycloalkanecarbonyl, —SO$_2$C$_{1-6}$ alkyl, —SO$_2$—C$_{3-6}$ cycloalkyl, SO$_2$NR$^e$R$^f$, pyridinoyl, $R^b$ is hydrogen, $C_{1-6}$ alkyl, aryl or pyridinyl.

In another embodiment of the present invention there is provided a compound according to formula I wherein $R^1$ is (alkylene)$_{0-6}$NR$^a$R$^b$, $R^a$ is optionally substituted aroyl, $R^b$ is hydrogen, $C_{1-6}$ alkyl, aryl or pyridinyl.

In yet another embodiment of the present invention there is provided a compound according to formula I wherein $R^1$ is (alkylene)$_{0-6}$NR$^a$R$^b$, $C_{3-7}$ cycloalkanecarbonyl, $R^b$ is hydrogen, $C_{1-6}$ alkyl, aryl or pyridinyl.

In a still another embodiment of the present invention there is provided a compound according to formula I wherein $R^1$ is (alkylene)$_{0-6}$NR$^a$R$^b$, $R^a$ is —SO$_2$C$_{1-6}$ alkyl, $R^b$ is hydrogen, $C_{1-6}$ alkyl, aryl or pyridinyl.

In another embodiment of the present invention there is provided a compound according to formula I wherein $R^1$ is (alkylene)$_{0-6}$NR$^a$R$^b$, $R^a$ is —SO$_2$—C$_{3-6}$ cycloalkyl, $R^b$ is hydrogen, $C_{1-6}$ alkyl, aryl or pyridinyl.

In a another embodiment of the present invention there is provided a compound according to formula I wherein $R^1$ is (alkylene)$_{0-6}$NR$^a$R$^b$, $R^a$ is optionally substituted aroyl, $C_{3-7}$ cycloalkanecarbonyl, —SO$_2$C$_{1-6}$ alkyl, SO$_2$NR$^e$R$^f$, pyridinoyl, $R^b$ is hydrogen, $C_{1-6}$ alkyl, aryl or pyridinyl.

In a fifth embodiment of the present invention there is provided a compound according to formula I wherein $R^1$ is (alkylene)$_{0-6}$NR$^a$R$^b$ and $R^a$ and $R^b$ together are S(=O)$_2$NR$^6$(CH$_2$)$_p$ wherein p is 3 to 5.

In a sixth embodiment of the present invention there is provided a compound according to formula I wherein $R^1$ is (alkylene)$_{0-3}$NR$^a$R$^b$ and $R^a$ and $R^b$ together are S(=O)$_2$NR$^6$(CH$_2$)$_p$ wherein p is 3 to 5, $R^2$ is hydrogen or $C_{1-6}$ alkoxy and $R^{3a}$, $R^{3b}$ and $R^{3c}$ are methyl.

In a seventh embodiment of the present invention there is provided a compound according to formula I wherein $R^1$ is (alkylene)$_{0-6}$NR$^a$R$^b$ and $R^a$ and $R^b$ together with the nitrogen to which they are attached are (a) phthaloyl, (b) 1-methyl-1,3-dihydro-2-oxo-benzoimidazol-3-yl, (c) 5-oxo-pyrrolidin-1-yl optionally substituted $C_{1-6}$ carboalkoxy, carboxy $C_{1-3}$ hydroxymethyl, (d) 3-hydroxymethyl-pyrrolidin-1-yl (e) 2-oxo-oxazolidin-3-yl optionally substituted with $C_{1-6}$ alkyl or (f) 3-oxo-2,3-dihydro-1H-isoindolyl optionally substituted with $C_{1-6}$ alkylsulfonylamino or $C_{3-6}$ cycloalkylsulfonylamino In an eighth embodiment of the present invention there is provided a compound according to formula I wherein $R^1$ is (alkylene)$_{0-6}$COX, X is $C_{1-6}$ alkoxy or NR$^c$R$^d$.

In an ninth embodiment of the present invention there is provided a compound according to formula I wherein $R^1$ is (alkylene)$_{0-3}$COX, X is $C_{1-6}$ alkoxy or NR$^c$R$^d$, $R^2$ is hydrogen or $C_{1-6}$ alkoxy and $R^{3a}$, $R^{3b}$ and $R^{3c}$ are methyl.

In a tenth embodiment of the present invention there is provided a compound according to formula I selected from the group consisting of compounds I-1 to I-91 and I-92 in Table I or a pharmaceutically acceptable salt thereof.

In a eleventh embodiment of the present invention there is provide a method of treating a disease caused by HCV in a patient in need thereof comprising administering a therapeutically effective amount of a compound according to formula I wherein $R^1$, $R^2$, $R^{3a}$, $R^{3b}$, $R^{3c}$, $R^4$, $R^5$, $R^6$, $R^a$, $R^b$, $R^c$, $R^d$, $R^e$, $R^f$, X, $X^1$, n and p are as defined herein above.

In a twelfth embodiment of the present invention there is provide a method of treating a disease caused by HCV in a patient in need thereof comprising co-administering a therapeutically effective amount of a compound according to formula I wherein $R^1$, $R^2$, $R^{3a}$, $R^{3b}$, $R^{3c}$, $R^4$, $R^5$, $R^6$, $R^a$, $R^b$, $R^c$, $R^d$, $R^e$, $R^f$, X, $X^1$, n and p are as defined herein above and at least one immune system modulator and/or at least one antiviral agent that inhibits replication of HCV.

In a thirteenth embodiment of the present invention there is provide a method of treating a disease caused by HCV in a patient in need thereof comprising co-administering a therapeutically effective amount of a compound according to formula I wherein $R^1$, $R^2$, $R^{3a}$, $R^{3b}$, $R^{3c}$, $R^4$, $R^5$, $R^6$, $R^a$, $R^b$, $R^c$, $R^d$, $R^e$, $R^f$, X, $X^1$, n and p are as defined herein above and at least one immune system modulator selected from interferon, interleukin, tumor necrosis factor or colony stimulating factor.

In a fourteenth embodiment of the present invention there is provide a method of treating a disease caused by HCV in a patient in need thereof comprising co-administering a therapeutically effective amount of a compound according to formula I wherein $R^1$, $R^2$, $R^{3a}$, $R^{3b}$, $R^{3c}$, $R^4$, $R^5$, $R^6$, $R^a$, $R^b$, $R^c$, $R^d$, $R^e$, $R^f$, X, $X^1$, n and p are as defined herein above and an interferon or chemically derivatized interferon.

In a fifteenth embodiment of the present invention there is provide a method of treating a disease caused by HCV in a patient in need thereof comprising co-administering a therapeutically effective amount of a compound according to formula I wherein $R^1$, $R^2$, $R^{3a}$, $R^{3b}$, $R^{3c}$, $R^4$, $R^5$, $R^6$, $R^a$, $R^b$, $R^c$, $R^d$, $R^e$, $R^f$, X, $X^1$, n and p are as defined herein above and another antiviral compound selected from the group consisting of a HCV protease inhibitor, another HCV polymerase inhibitor, a HCV helicase inhibitor, a HCV primase inhibitor and a HCV fusion inhibitor.

In a sixteenth embodiment of the present invention there is provided a method of inhibiting the replication of HCV in a cell comprising administering a therapeutically effective amount of a compound according to formula I wherein $R^1$, $R^2$, $R^{3a}$, $R^{3b}$, $R^{3c}$, $R^4$, $R^5$, $R^6$, $R^a$, $R^b$, $R^c$, $R^d$, $R^e$, $R^f$, X, $X^1$, n and p are as defined herein above.

In a seventeenth embodiment of the present invention there is provided a composition containing a therapeutically effective amount of a compound according to formula I wherein $R^1$, $R^2$, $R^{3a}$, $R^{3b}$, $R^{3c}$, $R^4$, $R^5$, $R^6$, $R^a$, $R^b$, $R^c$, $R^d$, $R^e$, $R^f$, X, $X^1$, n and p are as defined herein above admixed with at least one pharmaceutically acceptable carrier, diluent or excipient.

The term "alkyl" as used herein without further limitation denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl" (or "arylalkyl") or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het) arylalkyl" or "(het)aralkyl" are interpreted similarly except R' is optionally an aryl or a heteroaryl radical. The term "pyridinyl $C_{1-6}$ alkyl refers to a group wherein R' is pyridinyl and R" is alkylene.

The term "alkylene" as used herein denotes a divalent saturated linear hydrocarbon radical of 1 to 10 carbon atoms (e.g., (CH2)n) or a branched saturated divalent hydrocarbon radical of 2 to 10 carbon atoms (e.g., —CHMe- or —CH$_2$CH (i-Pr)CH$_2$—), unless otherwise indicated. "$C_{0-4}$ alkylene" refers to a linear or branched saturated divalent hydrocarbon radical comprising 1-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "aryl" as used herein denotes a phenyl radical which can be optionally substituted with one or more, preferably one or three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylaminosulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated. Alternatively two adjacent atoms of the aryl ring may be substituted with a methylenedioxy or ethylenedioxy group.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "cycloalkylalkyl" as used herein refers to the radical R'R"—, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cycloalkyl and R" is $C_{1-3}$ alkylene as defined herein.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The terms "alkoxycarbonyl" and "aryloxycarbonyl" as used herein denotes a group of formula —C(=O)OR wherein R is alkyl or aryl respectively and alkyl and aryl are as defined herein. For example, $C_1$ alkoxycarbonyl refers to —C(=O)Me.

The term "haloalkoxy" as used herein refers to a group —OR where R is haloalkyl as defined herein. The term "haloalkylthio" as used herein refers to a group —SR where R is haloalkyl as defined herein.

The terms "hydroxyalkyl", "alkoxyalkyl", "acyloxyalkyl" or "cyanoalkyl" as used herein denote an alkyl radical as herein defined wherein one to three hydrogen atoms on different carbon atoms is/are replaced by hydroxyl, alkoxy, acyloxy or cyano groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom.

The terms "hydroxyalkoxy" and "alkoxyalkoxyl" as used herein denotes alkoxy radical as herein defined wherein one to three hydrogen atoms on different carbon atoms is/are replaced by hydroxyl or alkoxy groups respectively. A $C_{1-3}$ alkoxy-$C_{1-6}$ alkoxy moiety refers to a $C_{1-6}$ alkoxy substituent in which 1 to 3 hydrogen atoms are replaced by a $C_{1-3}$ alkoxy and the point of attachment of the alkoxy is the oxygen atom.

The term "$C_{1-6}$ fluoroalkyl" as used herein denotes a unbranched or branched chain alkyl group as defined above wherein 1, 2, 3 or more hydrogen atoms are substituted by a fluorine.

The term "halogen" or "halo" as used herein means fluorine, chlorine, bromine, or iodine.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 1 to 6 carbon atoms. The $C_1$ acyl group is the formyl group wherein R=H and a $C_6$ acyl group refers to hexanoyl when the alkyl chain is unbranched. The term "arylcarbonyl" or "aroyl" as used herein means a group of formula C(=O)R wherein R is an aryl group; the term "benzoyl" as used herein an "arylcarbonyl" or "aroyl" group wherein R is phenyl. The term "pyridinoyl" refers to a moiety of formula (i):

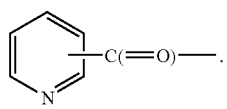

The terms "amino", "alkylamino" and "dialkylamino" as used herein refer to —$NH_2$, —NHR and —$NR_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to $NH_2$(alkylene)-, RHN(alkylene)-, and $R_2N$(alkylene)-respectively wherein R is alkyl, and both alkylene and alkyl are as defined herein. "$C_{1-10}$ alkylamino" as used herein refers to an aminoalkyl wherein alkyl is $C_{1-10}$. $C_{1-10}$ alkyl-amino-$C_{2-6}$ alkyl" as used herein refers to a C1-10 alkylamino(alkylene)$_{2-6}$ wherein alkyl is $C_{1-10}$ and the alkylene is $(CH_2)_{2-6}$. When the alkylene group contains three or more carbon atoms, the alkylene can be linear, e.g. —$(CH_2)_4$— or branched, e.g., —$(CMe_2CH_2)$—. The term "phenylamino" as used herein refers to —NHPh wherein Ph represents an optionally substituted phenyl group.

The term "$C_{1-3}$ acylamino-$C_{1-3}$ alkyl" as used herein refers a $(CH_2)_{1-3}$NHC(=O)R where R is hydrogen, methyl or ethyl The terms "alkylsulfonyl" and "arylsulfonyl" as used herein denotes a group of formula —$S(=O)_2R$ wherein R is alkyl or aryl respectively and alkyl and aryl are as defined herein. The term $C_{1-3}$ alkyl sulfonylamido as used herein refers to a group RSO2NH— wherein R is a $C_{1-3}$ alkyl group as defined herein.

The term "sulfamoyl" as used herein refers to the radical —$S(O)_2NH_2$. The terms "N-alkylsulfamoyl" and "N,N-dialkylsulfamoyl" as used herein refers to the radical —$S(O)_2$NR'R", wherein R' and R" are hydrogen and lower alkyl and R' and R" are independently lower alkyl respectively. Examples of N-alkylsulfamoyl substituents include, but are not limited to methylaminosulfonyl, iso-propylaminosulfonyl. Examples of N,N-dialkylsulfamoyl substituents include, but are not limited to dimethylaminosulfonyl, iso-propylmethylaminosulfonyl. The prefix N-alkyl or N,N-dialkyl can be replaced with aryl, heteroaryl, heterocyclyl or other radical to indicate a case where the amine is substituted with a group other than alkyl. The term "sulfamide" refers to a group $NH_2SO_2NH_2$. Sulfamides can be substituted on either of the nonequivalent nitrogen atoms and are distinguished as N or N' substituted sulfamides. A radical, —$NHSO_2NH_2$, is referred to herein as a "sulfamoylamino" radical. If it is necessary to distinguish specifically, —$NHSO_2N'R_2$ the nitrogen atom which is not linked to the core structure is designated N'. Thus N'-methyl sulfamoylamino refers to —$NHSO_2NHMe$, N-methyl sulfamoylamino refers to —$NMeSO_2NH_2$ and N,N'-dimethyl sulfamoylamino refers to —$NMeSO_2NHMe$. In there is no designation, either nitrogen can be substituted.

The term "alkylsulfonamido" refers to the radical —NH—$S(O)_2$-alkyl. The term alkyl can be replaced by other chemically relevant radicals such as aryl or heteroaryl to indicate, e.g. phenylsulfonamido —NH—$S(O)_2$-Ph. Thus "$C_{1-6}$ alkylsulfonamido" represents —NH—$S(O)_2$—$C_{1-6}$ alkyl "N-alkylalkylsulfonamido" refers to the radical —NR—$S(O)_2$-alkyl where R is a lower alkyl group.

The term "$C_{1-6}$ alkylsulfonamido-$C_{1-3}$ alkyl-" refers to the radical —NRH—$S(O)_2$—$C_{1-6}$ alkyl wherein R represents $(CH_2)_{1-3}$. The term alkyl can be replaced by other chemically relevant radicals such as aryl or heteroaryl to indicate, e.g. phenylsulfonamido —NH—$S(O)_2$-Ph. "N-alkylalkylsulfonamido" refers to the radical —NR—$S(O)_2$-alkyl where R is a lower alkyl group.

The term "carbamoyl" as used herein means the radical —$CONH_2$. The prefix "N-alkylcabamoyl" and "N,N-dialkylcarbamoyl" means a the radical CONHR' or CONR'R" respectively wherein the R' and R" groups are independently alkyl as defined herein. The prefix N-arylcarbamoyl" denotes the radical CONHR' wherein R' is an aryl radical as defined herein.

The term "heterocyclyl" or "heterocycle" as used herein denotes a monovalent saturated monocyclic radical, consisting of three to eight atoms per ring, incorporating one or more ring heteroatoms (chosen from N, O or S(O)0-2), and which can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Unless otherwise indicated the term "heterocyclyl" or "heterocycle refers to azetidinyl, pyrrolidinyl, hexahydroazepinyl, oxetanyl, tetrahydrofuranyl, tetrahydrothiophenyl, morpholinyl, piperidinyl, tetrahydropyranyl, thiomorpholinyl, and imidazolinyl moieties The terms "azetidine" ("azetidinyl"), "pyrrolidine" ("pyrrolidinyl"), "piperidine" ("piperidinyl") and "azepine" refer to a 4-, 5-, 6- or 7-membered cycloalkane respectively wherein one carbon atom is replaced by a nitrogen atom. The term "morpholine" refers to cyclohexane ring in which the 1 and 4 carbon atoms are replace by nitrogen and oxygen. "Thiomorpholine" refers to cyclohexane ring in which the 1 and 4 carbon atoms are replace by nitrogen and sulfur. The terms "oxetane" (oxetanyl), "tetrahydrofuran" (tetrahydrofuranyl) and "tetrahydropyran" (tetrahydropyranyl") refer to a four, five and six-membered non-fused heterocyclic ring respectively, each containing one oxygen atom.

The term pyridinyl-$C_{1-6}$ alkyl refers to a substitutent with the following formula:

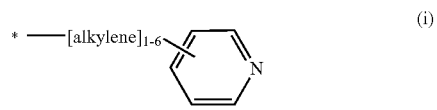

Compounds of the present invention and their isomeric forms and pharmaceutically acceptable salts thereof are also useful in treating viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and antiinfective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as an additional combination therapy with at least one of the compounds of the present invention.

In one embodiment, the compounds of the present invention according to formula I are used in combination with other active therapeutic ingredients or agents to treat patients with an HCV viral infection. According to the present invention, the active therapeutic ingredient used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, nucleoside inhibitors of HCV polymerase, non-nucleoside inhibitors of HCV polymerase, and other drugs for treating HCV, or mixtures thereof.

Examples of the nucleoside NS5b polymerase inhibitors include, but are not limited to NM-283, valopicitabine, R1626, PSI-6130 (R1656), IDX184 and IDX102 (Idenix) BILB 1941.

Examples of the non-nucleoside NS5b polymerase inhibitors include, but are not limited to HCV-796 (ViroPharma and Wyeth), MK-0608, MK-3281 (Merck), NM-107, R7128 (R4048), VCH-759, GSK625433 and GSK625433 (Glaxo), PF-868554 (Pfizer), GS-9190 (Gilead), A-837093 and A848837 (Abbot Laboratories), ANA598 (Anadys Pharmaceuticals); GL100597 (GNLB/NVS), VBY 708 (ViroBay), benzimidazole derivatives (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1), benzo-1,2,4-thiadiazine derivatives (D. Dhanak et al. WO 01/85172 A1, filed May 10, 2001; D. Chai et al., WO2002098424, filed Jun. 7, 2002, D. Dhanak et al. WO 03/037262 A2, filed Oct. 28, 2002; K. J. Duffy et al. WO03/099801 A1, filed May 23, 2003, M. G. Darcy et al. WO2003059356, filed Oct. 28, 2002; D. Chai et al. WO 2004052312, filed Jun. 24, 2004, D. Chai et al. WO2004052313, filed Dec. 13, 2003; D. M. Fitch et al., WO2004058150, filed Dec. 11, 2003; D. K. Hutchinson et al. WO2005019191, filed Aug. 19, 2004; J. K. Pratt et al. WO 2004/041818 A1, filed Oct. 31, 2003), 1,1-dioxo-4H-benzo[1,4]thiazin-3-yl derivatives (J. F. Blake et al. in U.S. Patent Publication US20060252785 and 1,1-dioxo-benzo[d]isothazol-3-yl compounds (J. F. Blake et al. in U.S. Patent Publication 2006040927).

Examples of the HCV NS3 protease inhibitors include, but are not limited to SCH-503034 (Schering, SCH-7), VX-950 (telaprevir, Vertex), BILN-2065 (Boehringer-Ingelheim, BMS-605339 (Bristo Myers Squibb), and ITMN-191 (Intermune).

Examples of the interferons include, but are not limited to pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen and actimmune, IFN-omega with DUROS, albuferon, locteron, Albuferon, Rebif, oral interferon alpha, IFNalpha-2b XL, AVI-005, PEG-Infergen, and pegylated IFN-beta.

Ribavirin analogs and the ribavirin prodrug viramidine (taribavirin) have been administered with interferons to control HCV.

Commonly used abbreviations include: acetyl (Ac), aqueous (aq.), atmospheres (Atm), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,5-diazabicyclo[4.3.0]non-5-ene (DBN), 1,8-diazabicyclo[5.4.0]undec-7-ene (DBU), N,N'-dicyclohexyl-carbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), $MeSO_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), satd. (saturated), tert-butyldimethylsilyl or t-$BuMe_2Si$ (TBDMS), triethylamine (TEA or $E_{t3}N$), triflate or $CF_3SO_2$-(TO, trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n-), iso (i-), secondary (sec-), tertiary (tert-) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

Examples of representative compounds encompassed by the present invention and within the scope of the invention are provided in the following Table. These examples and the preparations which follow are provided to enable those skilled in the art to more clearly understand and to practice the present invention. They should not be considered as limiting the scope of the invention, but merely as being illustrative and representative thereof.

Compounds encompassed by the present invention are substituted 3-phenyl-1H-pyridin-2-one derivatives. The following numbering scheme is used to refer to the substitution sites on the core substructure.

TABLE I

| Cpd. No. | R¹ | R² | R³ | R⁵ | ms | mp | IC$_{50}$[1] |
|---|---|---|---|---|---|---|---|
| I-1 | —(CH$_2$)$_2$CO$_2$H | OMe | CMe$_3$ | H | 330 | | 0.273 |
| I-2 | —CH$_2$OH | OMe | CMe$_3$ | H | 288 | 215.0-216.0 | 1.01 |
| I-3 | —(CH$_2$)$_2$CO$_2$Me | OMe | CMe$_3$ | H | 344 | | 0.954 |
| I-4 | —CO$_2$H | OMe | CMe$_3$ | H | 302 | 244.0-245.0 | 0.027 |
| I-5 | —(CH$_2$)$_2$OH | OMe | CMe$_3$ | H | 302 | 231.8-233.7 | 1.58 |
| I-6 | —NHSO$_2$Me | H | CMe$_3$ | H | 321 | 219.3-233.8 | 3.85 |
| I-7 | —CH$_2$CO$_2$H | OMe | CMe$_3$ | H | 316 | | 0.156 |
| I-8 | —NHAc | H | CMe$_3$ | H | 285 | 259.0-260.0 | 8.56 |
| I-9 | —CONHMe | OMe | CMe$_3$ | H | 315 | | 0.442 |
| I-10 | —CH$_2$CONHMe | OMe | CMe$_3$ | H | 329 | | 0.70 |
| I-11 | —CH$_2$CONH$_2$ | OMe | CMe$_3$ | H | 315 | | 0.437 |
| I-12 | —CH$_2$NHAc | OMe | CMe$_3$ | H | 329 | | 0.125 |
| I-13 | —CH$_2$NHSO$_2$Me | OMe | CMe$_3$ | H | 365 | | 0.064 |
| I-14 | —CH$_2$N(Me)Ac | OMe | CMe$_3$ | H | 343 | | 0.151 |
| I-15 | —CH$_2$SO$_2$Me | OMe | CMe$_3$ | H | 350 | | 0.746 |
| I-16 | (2-ethyl-1,1-dioxo-1,2-thiazinane) | OMe | CMe$_3$ | H | 405 | 225.8-226.1 | 0.035 |
| I-17 | —(CH$_2$)$_2$NHSO$_2$Me | OMe | CMe$_3$ | H | 379 | 219.3-222.4 | 0.28 |
| I-18 | (2-oxopyrrolidin-1-yl)ethyl | OMe | CMe$_3$ | H | 355 | | 0.121 |
| I-19 | 2-(4-chlorophenylsulfonyl)ethyl | OMe | CMe$_3$ | H | 407 | 237.0-238.0 | 0.173 |
| I-20 | —CH$_2$NHSO$_2$CH$_2$Ph | OMe | CMe$_3$ | H | 441 | 249.0-250.0 | 0.211 |
| I-21 | (1,1-dioxoisothiazolidin-2-yl)ethyl | OMe | CMe$_3$ | H | 391 | 109.4-126.9 | 0.017 |
| I-22 | —CH$_2$N(Me)COPh | OMe | CMe$_3$ | H | 405 | 236.2-238.0 | 0.025 |

TABLE I-continued

| Cpd. No. | R¹ | R² | R³ | R⁵ | ms | mp | IC₅₀¹ |
|---|---|---|---|---|---|---|---|
| I-23 | 1-(2-oxopiperidinyl)ethyl | OMe | CMe₃ | H | 369 | 224.6-228.9 | 0.052 |
| I-24 | —CH₂NHSO₂Et | OMe | CMe₃ | H | 379 | 118.0-120.0 | |
| I-25 | —CH₂NHSO₂-i-Pr | OMe | CMe₃ | H | 393 | 118.0-120.0 | 0.183 |
| I-26 | —CH₂N(CH₂Ph)SO₂Me | OMe | CMe₃ | H | 455 | 229.0-230.0 | 0.145 |
| I-27 | —CH₂N(Et)SO₂Me | OMe | CMe₃ | H | 393 | 245.0-246.0 | 0.044 |
| I-28 | —CH₂N(i-Pr)SO₂Me | OMe | CMe₃ | H | 407 | 285.0-286.0 | 0.033 |
| I-29 | 1-(2,5-dioxopyrrolidinyl)ethyl | OMe | CMe₃ | H | 369 | 112.2-124.9 | 0.068 |
| I-30 | —CH₂N(SO₂Me)CH₂CH₂OAc | OMe | CMe₃ | H | 451 | 207.0-208.0 | 0.035 |
| I-31 | —CH₂N(SO₂Me)CH₂-(pyrrolidin-3-yl) | OMe | CMe₃ | H | 448 | 158.0-160.0 | 0.097 |
| I-32 | —(CH₂)₂N(n-Bu)SO₂Me | OMe | CMe₃ | H | 421 | 214.0-216.0 | 0.086 |
| I-33 | 2-(1,3-dioxoisoindolinyl)ethyl | OMe | CMe₃ | H | 417 | 277.0-280.0 | 0.035 |
| I-34 | —CH₂N(Ph)SO₂Me | OMe | CMe₃ | H | 441 | 226.0-227.0 | 0.013 |
| I-35 | —CH₂N(SO₂Me)CH₂CH₂OH | OMe | CMe₃ | H | 409 | 234.7-236.0 | 0.026 |

TABLE I-continued

| Cpd. No. | R¹ | R² | R³ | R⁵ | ms | mp | IC$_{50}$[1] |
|---|---|---|---|---|---|---|---|
| I-36 | —NHCOPh | OMe | CMe₃ | H | 390 | 145.0-150.0 | 0.019 |
| I-37 | —CH₂NHSO₂Me | OMe | CMe₃ | 6-Me | 379 | 120.0-125.0 | 0.146 |
| I-38 | *-CH₂-NH-C(=O)-C₆H₄-OH (4-hydroxybenzamide) | OMe | CMe₃ | H | 407 | 205.0-210.0 | 0.016 |
| I-39 | *-CH₂-N(3,3-diethyl-2,4-dioxo-dihydropyridinyl) | OMe | CMe₃ | H | 437 | 282.0-284.0 | 0.159 |
| I-40 | *-C(=O)-N(morpholinyl) | OMe | CMe₃ | H | 371 | 208.0-210.0 | 0.533 |
| I-41 | —CONMe₂ | OMe | CMe₃ | H | 329 | 208.0-210.0 | 1.685 |
| I-42 | *-CH₂-NH-C(=O)-C₆H₄-NH₂ | OMe | CMe₃ | H | 406 | 165.0-167.0 | 0.036 |
| I-43 | *-CH₂-NH-C(=O)-C₆H₄-NHSO₂Me | OMe | CMe₃ | H | 484 | 175.0-180.0 | 0.05 |
| I-44 | *-CH₂-NH-C(=O)-C₆H₄-N(SO₂Me)₂ | OMe | CMe₃ | H | 562 |  | 0.774 |
| I-45 | —CH₂NHSO₂Me | OMe | CMe₃ | 5-F | 383 |  | 0.687 |

TABLE I-continued (I)

| Cpd. No. | R¹ | R² | R³ | R⁵ | ms | mp | IC$_{50}$[1] |
|---|---|---|---|---|---|---|---|
| I-46 | *-C(O)-N(piperazinyl)-NAc | OMe | CMe$_3$ | H | 412 | 206.0-208.0 | 0.615 |
| I-47 | *-C(O)-N(Me)-CH$_2$CH$_2$OMe | OMe | CMe$_3$ | H | 373 | 160.0-162.0 | 1.51 |
| I-48 | *-CH$_2$-N(SO$_2$Me)-CH$_2$-(N-Ac-pyrrolidinyl) | OMe | CMe$_3$ | H | 490 | 196.0-198.0 | 0.084 |
| I-49 | *-CH$_2$-NH-C(O)-(3-pyridyl) | OMe | CMe$_3$ | H | 392 |  | 0.026 |
| I-50 | —CH$_2$NHSO$_2$NH$_2$ | OMe | CMe$_3$ | H | 366 |  | 0.049 |
| I-51 | *-C(O)-N(thiomorpholinyl-1,1-dioxide) | OMe | CMe$_3$ | H | 419 | 252.0-254.0 | 0.552 |
| I-52 | —CH(Me)NHSO$_2$Me | OMe | CMe$_3$ | H | 379 | 284.0-286.0 | 0.654 |
| I-53 | —CH(Me)N(Me)SO$_2$Me | OMe | CMe$_3$ | H | 393 | 205.0-207.0 | 0.187 |
| I-54 | —CO$_2$Et | OMe | CMe$_3$ | H | 330 | 214.0-215.0 | 0.039 |
| I-55 | *-CH$_2$-N(SO$_2$-i-Pr)-CH$_2$-cyclobutyl | OMe | CMe$_3$ | H | 461 | 206.0-208.0 | 0.131 |
| I-56 | *-C(O)-N(4-cyanopiperidinyl) | OMe | CMe$_3$ | H | 394 | 213.0-215.0 | 0.432 |

TABLE I-continued

Structure (I): 3-aryl-pyridin-2(1H)-one core with R⁵ substituents on pyridinone ring (position p), and R¹ (ortho), R² (para), R³ (meta) on phenyl ring.

| Cpd. No. | R¹ | R² | R³ | R⁵ | ms | mp | IC₅₀¹ |
|---|---|---|---|---|---|---|---|
| I-57 | -CH₂-(4-piperidinyl)-N(SO₂Me)(Et) | OMe | CMe₃ | H | 448 | 205.0-208.0 | 0.057 |
| I-58 | -CH₂-N(Me)-C(O)-CH₂-(4-pyridyl) | OMe | CMe₃ | H | 406 | 199.0-201.0 | 1.14 |
| I-59 | -CH₂-NH-(2-pyridyl) | OMe | CMe₃ | H | 392 | 247.0-249.0 | 0.617 |
| I-60 | -CH₂-[1,2,5-thiadiazolidine 1,1-dioxide-2-yl] (NH free) | OMe | CMe₃ | H | 393 | 230.0-231.0 | 0.023 |
| I-61 | -CH₂-[1,2,5-thiadiazolidine 1,1-dioxide-2-yl]-N(5)-C(O)OCMe₃ | OMe | CMe₃ | H | 492 | 125.0-127.0 | 0.319 |
| I-62 | -C(O)-N(4,4-difluoropiperidin-1-yl) | OMe | CMe₃ | H | 405 | 223.0-224.0 | 0.955 |
| I-63 | -CH₂-NH-C(O)-(3-NHSO₂Me-phenyl) | OMe | CMe₃ | H | 484 | 259.0-260.0 | 0.012 |

TABLE I-continued

| Cpd. No. | R¹ | R² | R³ | R⁵ | ms | mp | IC$_{50}$[1] |
|---|---|---|---|---|---|---|---|
| I-64 | (methyl-ethyl cyclic sulfamide) | OMe | CMe$_3$ | H | 406 | 253.0-255.0 | 0.060 |
| I-65 | N-ethyl-N-methyl 3-(NHSO$_2$Me)benzamide | OMe | CMe$_3$ | H | 498 | 170.0-172.0 | 0.013 |
| I-66 | —CON(Me)CH$_2$CN | OMe | CMe$_3$ | H | 354 | 211.0-212.0 | 0.152 |
| I-67 | 4-(2-methoxyethyl)piperazine-1-carbonyl | OMe | CMe$_3$ | H | 428 | 179.0-181.0 | 3.69 |
| I-68 | 3-hydroxyazetidine-1-carbonyl | OMe | CMe$_3$ | H | 357 | 236.0-238.0 | 0.211 |
| I-69 | 3-methyl-2-oxo-2,3-dihydrobenzimidazol-1-yl-ethyl | OMe | CMe$_3$ | H |  | 140.0-142.0 | 0.034 |
| I-70 | 2-(ethoxycarbonyl)-5-oxopyrrolidin-1-yl-ethyl | OMe | CMe$_3$ | H | 427 | 92.0-95.0 | 0.07 |

TABLE I-continued

| Cpd. No. | R¹ | R² | R³ | R⁵ | ms | mp | IC$_{50}$[1] |
|---|---|---|---|---|---|---|---|
| I-71 | (1-ethyl-5-oxopyrrolidin-2-yl)-CO₂H | OMe | CMe₃ | H | 399 | 199.0-200.0 | 0.036 |
| I-72 | (1-ethyl-5-oxopyrrolidin-2-yl)-CH₂OH | OMe | CMe₃ | H | 385 | 146.0-148.0 | 0.077 |
| I-73 | acyl-3-(hydroxymethyl)pyrrolidine | OMe | CMe₃ | H | 385 | 201.0-203.0 | 1.61 |
| I-74 | (3-ethyloxazolidin-2-one) | OMe | CMe₃ | H |  |  | 0.056 |
| I-75 | (3-ethyl-4-isopropyloxazolidin-2-one) | OMe | CMe₃ | H | 399 |  | 0.086 |
| I-76 | (3-ethyl-4-isopropyloxazolidin-2-one) | OMe | CMe₃ | H | 399 |  | 0.134 |

TABLE I-continued

| Cpd. No. | R¹ | R² | R³ | R⁵ | ms | mp | IC$_{50}$[1] |
|---|---|---|---|---|---|---|---|
| I-77 | C(O)N(Me)CH₂-(4-F-C₆H₄) | OMe | CMe₃ | H | 423 | 218.0-220.0 | 0.611 |
| I-78 | C(O)-morpholin-4-yl-2-CH₂OH | OMe | CMe₃ | H | 401 | | 1.41 |
| I-79 | C(O)-piperidin-1-yl-4-OPh | OMe | CMe₃ | H | 461 | | 1.32 |
| I-80 | —CONH₂ | OMe | CMe₃ | H | 302 | 215.0-216.0 | 0.068 |
| I-81 | C(O)NH-CH₂-(cyclopentyl-3-NHSO₂Me) | OMe | CMe₃ | H | 476 | 158.0-160.0 | 0.022 |
| I-82 | C(O)NH-CH₂-(cyclohexyl-3-NHSO₂Me) | OMe | CMe₃ | H | 490 | 162.0-164.0 | 0.03 |
| I-83 | CH₂-(2-oxo-5-(CH₂OH)-pyrrolidin-1-yl) | OMe | CMe₃ | H | 385 | 150.0-152.0 | 0.146 |

TABLE I-continued

Structure with numbered pyridinone-phenyl system (positions 1-5 on pyridinone N-C=O ring; positions 2-6 on phenyl).

General structure (I): pyridinone with NH, C=O, $(R^5)_p$ substituents, connected to phenyl bearing $R^1$, $R^2$, $R^3$.

| Cpd. No. | R¹ | R² | R³ | R⁵ | ms | mp | IC₅₀¹ |
|---|---|---|---|---|---|---|---|
| I-84 | [pyrrolidine-2-carboxamide with 4-NHSO₂Me] | OMe | CMe₃ | H | | 178.0-180.0 | 0.169 |
| I-85 | —CONHCH₂CN | OMe | CMe₃ | H | 340 | | 0.023 |
| I-86 | —CH₂N(Me)SO₂Me | OMe | CMe₃ | H | 379 | 230.0-231.0 | 0.052 |
| I-87 | [CH₂-N(SO₂-2-chlorophenyl)] | OMe | CMe₃ | H | 461 | 231.0-232.0 | 0.358 |
| I-88 | [CH₂-N(4,4-dimethyl-2,6-dioxopiperidinyl)] | OMe | CMe₃ | H | 411 | >300 | 0.052 |
| I-89 | —CH₂N(Ph)Ac | OMe | CMe₃ | H | 405 | | 0.106 |
| I-90 | [full structure: pyridinone connected to phenyl with CO₂Me, n-C₃H₇, OMe, CMe₃] | | | | 358 | | |
| I-91 | —CN | OMe | CMe₃ | H | 283 | 247.0-249.0 | 0.374 |
| I-92 | [isoindolin-1-one with 6-NHSO₂Me, N-CH₂-] | OMe | CMe₃ | H | | 173.0-175.0 | 0.008 |

¹IC₅₀ (μM) NS5B polymerase assay (Example 33)

Sulfonylated or acylated 3-(2-aminomethyl-5-tert-butyl-4-methoxy-phenyl)-1H-pyridin-2-one derivatives were prepared by sulfonylation or acylation of the benzyl amine A-3c. The requisite amine is prepared by bromination of (4-tert-butyl-3-methoxy-phenyl)-methanol (A-1a, available form the corresponding benzoic acid infra) with NBS or bromine Analogous bromination of 4-tert-butyl-3-methoxy-benzoic acid (see, e.g. example 31, CASRN 79822-46-1) or 4-tert-butyl-3-methoxy-phenylamine afforded the corresponding benzoic acid or aniline derivatives (CASRN 103273-01-4).

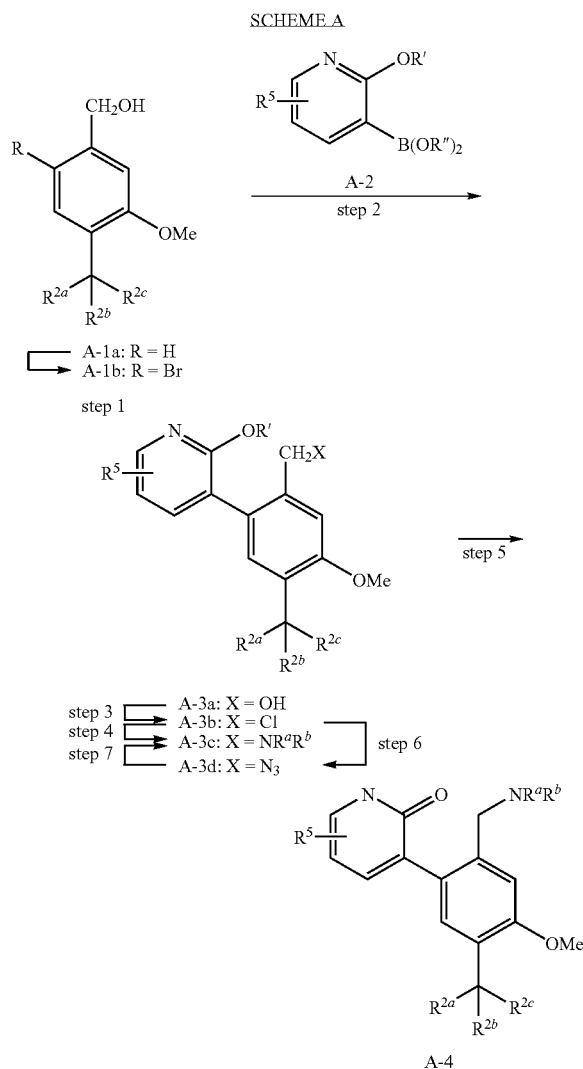

The compounds encompassed within the present claims are characterized by the presence of an optionally substituted 2-oxo-1,2-dihydro-pyridin-3-yl moiety. The pyridone can be introduced by a palladium-catalyzed Suzuki coupling of A-1b and an optionally substituted 2-alkoxy- or 2-benzyloxy-pyridin-3-yl boronic acid. The boronic acid can optionally be replaced by a 4,4,5,5-tetramethyl-[1,3,2]dioxaborolane or other ester of a boronic acid. The Suzuki reaction is a palladium-catalyzed coupling of a boronic acid with an aryl or vinyl halide or triflate. Typical catalysts include Pd(PPh$_3$)$_4$, PdCl$_2$(PPh$_3$)$_2$, Pd(OAc)$_2$ and PdCl$_2$(dppf). With PdCl$_2$(dppf), primary alkyl borane compounds can be coupled to aryl or vinyl halide or triflate without beta-elimination. The reaction can be carried out in a variety of organic solvents including toluene, THF, dioxane, DCE, DMF, DMSO, DCM, MeOH and MeCN, aqueous solvents and under biphasic conditions. Reactions are typically run from about RT to about 150° C. Additives (e.g., CsF, KF, TlOH, NaOEt and KOH) frequently accelerate the coupling. Although there are numerous components in the Suzuki reaction including the particular palladium catalyst, the ligand, additives, solvent, temperature, etc., numerous protocols have been identified. Highly active catalysts have been described (see, e.g., J. P. Wolfe et al., *J. Am. Chem. Soc.* 1999 121(41):9550-9561 and A. F. Littke et al., *J. Am. Chem. Soc.* 2000 122(17):4020-4028). One skilled in the art will be able to identify a satisfactory protocol without undue experimentation and furthermore that the position of the boronic acid and the leaving group can be reversed.

Conversion of the benzyl alcohol to a benzyl amine is typically carried out by conversion of the benzyl alcohol to a benzyl halide derivative which is subjected to displacement by azide and subsequent reduction of the azide to the amine A-3c. The azide reduction is generally accomplished with triphenylphosphine or a trialkylphosphine, but other procedures for the reduction of azides are well known. Numerous well known related sequences can be adopted which result in the formation of A-3c and any can be adopted to efficiently produce the claimed compounds. Sulfonylation or acylation of the benzylamine affords A-3c were NR$^a$R$^b$ comprises a sulfonamide or carboxamide respectively.

Finally the requisite pyridone is obtained by cleaving the pyridinyl O-methyl (or O-benzyl)ether then affords the requisite pyridone. While this is typically carried out in a mixture of HBr and HOAc when R' is methyl or by catalytic hydrogenolysis when R' is CH$_2$Ph, other suitable methods are known in the art and the selection of the procedures is merely a matter of convenience. While SCHEME A depicts a sequence wherein the pyridone ring is elaborated after introduction of the C-2 substituent, the sequence can in many cases be reversed and the sequence the transformations are carried out is typically a matter of convenience rather than necessity.

Alternatively, deprotonation of a sulfonamide or a carboxamide and alkylation of the benzyl halide, A-1b or A-3b, affords the compounds of the present invention. N-Alkylation of sulfonamides or amides is usually carried out under basic conditions well known to one skilled in the art. The reaction is typically carried out in aprotic solvents such as THF, DMF, DMSO, NMP and mixtures thereof at temperatures between −78° C. and 100° C. Typically used bases are sodium hydride, potassium hydride, sodium methoxide, potassium tert-butoxide, lithium hexamethyldisilazide, sodium hexamethyldisilazide, potassium hexamethyldisilazide. (Example 1 is exemplary.)

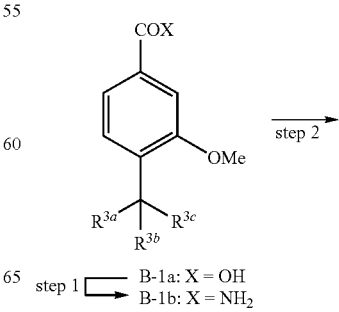

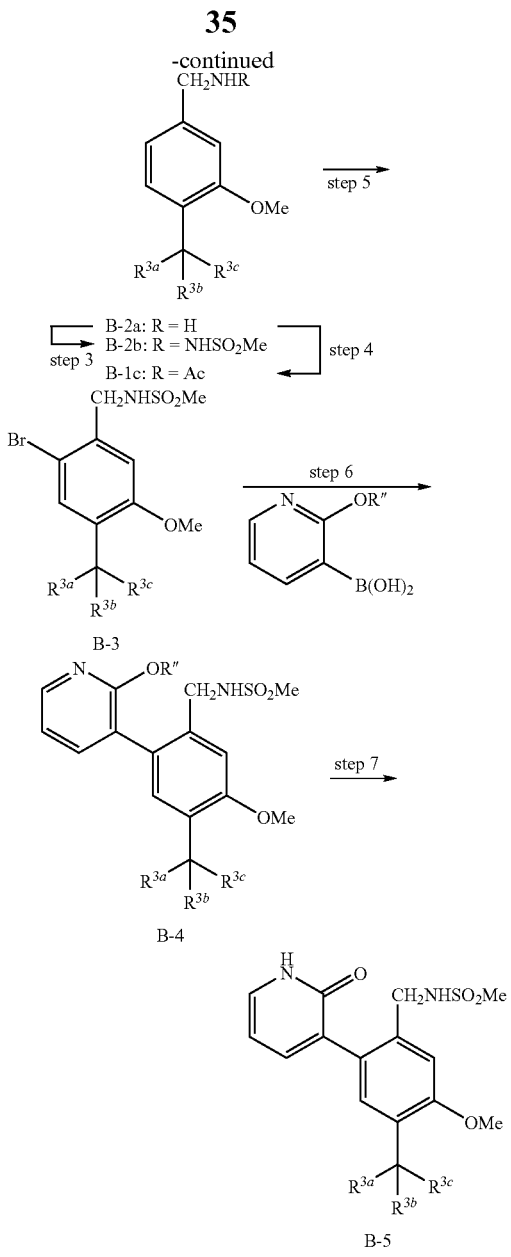

SCHEME B affords an alternative procedure in which the benzyl amine is prepared by conversion of a benzoic acid to the corresponding amide which in turn, can be reduced to the benzyl amine and further converted to compounds of the instant invention using procedures analogous to SCHEME A. It will be apparent to one skilled in the art that compounds such as B-1a or A-1b can be homologated using basic organochemical transformations. Thus oxidation of B-1b to the corresponding aldehyde and subjecting the aldehyde to a Wittig reaction with methoxymethyl triphenylphosphonium chloride affords an enol ether which is readily transformed to the corresponding phenylacetic acid derivative. (see, e.g., example 16) Three-carbon appendages are readily prepared by subjecting the aldehyde to Horner-Wadsworth-Emmons condensation with methyl triphenylphosphonoacetate followed by reduction of the olefin. (see, e.g., example 15) Benzyl halides such as A-3b can be similarly homologated by displacement with cyanide and subsequent hydrolysis of the nitrile. Compounds encompassed by the invention lacking the methoxy substituent are readily available from 2-bromo-4-tert-butyl-benzoic acid (CASRN 6332-96-3) or 2-bromo-4-tert-butyl-aniline (CASRN 103273-01-4) derivatives. Other transformations which are less generic to compounds encompassed by the invention can be found in the examples which follow.

Transformation of a carboxylic acid to an amide can be effected by preparing an activated carboxylic acid into a more reactive form such as an acid chloride or a symmetrical or mixed acid anhydride and reacting the activated derivative with an amines in a solvent such as DMF, DCM, THF, with or without water as a co-solvent, at temperatures between 0° and 60° C. generally in the presence of a base such as $Na_2CO_3$, $NaHCO_3$, $K_2CO_3$, DIPEA, TEA or pyridine and the like to afford an amide. Carboxylic acids are converted into their acid chlorides using standard reagents well known to someone skilled in the art, such as thionyl chloride, oxalyl chloride, phosphoryl chloride and the like. Those reagents can be used in presence of bases such as DIPEA, TEA or pyridine in inert solvent such as dichloromethane or dimethylformamide Sulfonylation is typically carried out analogously using a sulfonyl chloride and tertiary amine base.

Alternatively a carboxylic acid can be converted in situ into activated acids by different peptide coupling procedures known to those skilled in the art. These activated acids were reacted directly with the amines to afford amides. Said activation can involve the use of an activating agent like EDIC or DCC, HOBt, BOP, PyBrOP or 2-fluoro-1-methylpyridinium p-toluenesulphonate (Mukaiyama's reagent) and the like with or without a base such NMM, TEA or DIPEA in an inert solvent such as DMF or DCM at temperatures between 0° C. and 60° C. The reaction may alternatively be carried out in presence of O-(7-azabenzotriazol-1-yl)-N,N,N',N'-tetramethyluronium hexafluorophosphate (HATU) or 1-hydroxy-7-azabenzotriazole (HOAt) and TEA or DIPEA in DMF, DCM or THF. (*Organic Synthesis*, E. Winterfeldt, ed., vol. 6, Pergamon Press, Oxford 1991 pp. 381-411; see R. C. Larock, *Comprehensive Organic Transformations—A Guide to Functional Group Preparations,* 1989, VCH Publishers Inc., New York; pp. 972-976)

Anti-Viral Activity

The activity of the inventive compounds as inhibitors of HCV activity may be measured by any of the suitable methods known to those skilled in the art, including in vivo and in vitro assays. For example, the HCV NS5B inhibitory activity of the compounds of formula I can determined using standard assay procedures described in Behrens et al., *EMBO J.* 1996 15:12-22, Lohmann et al., *Virology* 1998 249:108-118 and Ranjith-Kumar et al., *J. Virology* 2001 75:8615-8623. Unless otherwise noted, the compounds of this invention have demonstrated in vitro HCV NS5B inhibitory activity in such standard assays. The HCV polymerase assay conditions used for compounds of the present invention are described in Example 3. Cell-based replicon systems for HCV have been developed, in which the nonstructural proteins stably replicate subgenomic viral RNA in Huh7 cells (V. Lohmann et al., *Science* 1999 285:110 and K. J. Blight et al., *Science* 2000 290:1972. The cell-based replicon assay conditions used for compounds of the present invention are described in Example 4. In the absence of a purified, functional HCV replicase consisting of viral non-structural and host proteins, our understanding of Flaviviridae RNA synthesis comes from studies using active recombinant RNA-dependent RNA-polymerases and validation of these studies in the HCV replicon system Inhibition of recombinant purified HCV polymerase with compounds in vitro biochemical assays may be validated using the replicon system whereby the polymerase exists within a replicase complex, associated with other viral and cellular polypeptides in appropriate stoichiometry. Demonstration of cell-based inhibition of HCV replication may be more predictive of in vivo function than demonstration of HCV NS5B inhibitory activity in vitro biochemical assays.

Dosage and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate. The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

Furthermore, the term "treatment" of a HCV infection, as used herein, also includes treatment of a disease or a condition associated with or mediated by HCV infection, or the clinical symptoms thereof.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

A therapeutically effective amount of a compound of the present invention, and optionally one or more additional antiviral agents, is an amount effective to reduce the viral load or achieve a sustained viral response to therapy. Useful indicators for a sustained response, in addition to the viral load include, but are not limited to liver fibrosis, elevation in serum transaminase levels and necroinflammatory activity in the liver. One common example, which is intended to be exemplary and not limiting, of a marker is serum alanine transminase (ALT) which is measured by standard clinical assays. In some embodiments of the invention an effective treatment regimen is one which reduces ALT levels to less than about 45 IU/mL serum.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLE 1

2-[4-tert-Butyl-5-methoxy-2-(2-oxo-1,2-dihydropyridin-3-yl)-benzyl]-isoindole-1,3-dione (I-33) (SCHEME A)

(4-tert-Butyl-3-methoxy-phenyl)-methanol (A-1a)—To a solution of 4-tert-butyl-3-methoxybenzoic acid (3.00 g, 14.40 mmol) in THF (60 mL) cooled to 5° C. was added dropwise a solution of $BH_3.Me_2S$ (2.0M in THF, 16.60 mL, 33.10 mmol). The reaction was allowed to stir for 24 h at RT then cooled to −50° C. and quenched by dropwise addition of MeOH (20 mL). The reaction mixture was warmed to RT and concentrated in vacuo. The residue was taken up in MeOH (3×20 mL) and concentrated in vacuo. The final residue partitioned between EtOAc and satd. aqueous $NaHCO_3$. The organic layer was washed with water, brine, dried ($MgSO_4$), filtered and concentrated to afford 2.64 g (95%) of A-1a ($R^{2a}=R^{2b}=R^{2c}$=Me) as a colorless oil.

step 1—To a solution of A-1a (2.08 g, 10.70 mmol) in $CCl_4$ (75 mL) was added NBS (2.10 g, 11.80 mmol). The reaction was stirred for 15 min then diluted with a cold 10% aqueous $NaHSO_3$. The reaction mixture was extracted with DCM. The organic extract was washed with brine, dried ($MgSO_4$), filtered and concentrated. The residue was taken up in hexanes (80 mL) and then concentrated to afford 2.9 g (100%) of A-1b as a white solid.

step 2—A tube was charged with A-1b (750 mg, 2.75 mmol), A-2 (840 mg, 5.50 mmol, R'=OMe, R"=$R^5$=H), $Na_2CO_3$ (582 mg, 5.50 mmol) and $Pd(PPh_3)_4$ (320 mg, 0.275 mmol) in a mixture of MeOH (6 mL), and DCM (2 mL) sealed and irradiated in a microwave synthesizer at 120° C. for 25 min. The reaction was filtered through a pad of CELITE® and the filtrate was concentrated under reduced pressure. The crude residue was purified by $SiO_2$ chromatography eluting with a EtOAc/hexane gradient (10 to 35% EtOAc) to afford 0.670 g (81%) of A-3a.

step 3—A mixture of A-3a (670 mg, 2.23 mmol) and $SOCl_2$ (2.10 mL, 2.90 mmol) in chloroform (20 mL) was heated at reflux for 1 h and then at 40° C. for 40 min. The reaction was cooled to RT then concentrated in vacuo. The residue was partitioned between EtOAc and cold aqueous $NaHCO_3$. The organic layer was washed with water, brine, dried (MgSO4), filtered and concentrated to afford 0.660 g (93%) of A-3b.

step 4—To a mixture of phthalimide (17 mg, 0.11 mmol) in DMF (1.5 mL) cooled to 0° C. was added NaH (60% in oil dispersion, 5 mg, 0.12 mmol). The reaction mixture was stirred for 30 min. To the solution was added NaI (14 mg, 0.094 mmol) followed by A-3b (30 mg, 0.094 mmol). The resulting mixture was heated at 65° C. for 17 h then cooled to RT, quenched with a saturated aq $NH_4Cl$ and then extracted with EtOAc. The organic extract was washed sequentially with water and brine, dried ($MgSO_4$), filtered and concentrated. The crude residue was purified on a preparative TLC plated developed with 60% EtOAc in hexanes to afford 0.020 g (50%) of A-3c ($NR^aR^b$=phthalimide).

step 5—A mixture of A-3c (20 mg, 0.046 mmol), 48% HBr (0.10 mL) and HOAc (3 mL) in a sealed tube was heated at 65° C. for 17 h. The reaction mixture was cooled to RT, carefully poured into a saturated aq $NaHCO_3$, and extracted with EtOAc. The combined extracts were washed with brine, dried ($MgSO_4$), filtered and concentrated. The crude residue was purified on a preparative TLC plate developed with 6% MeOH/DCM to afford 0.017 g (88%) of I-33.

The following are prepared analogously by displacement of A-3b with the anion derived from deprotonation of the amide or sulfonamide in parentheses: I-29 (pyrrolidine-2,5-dione), I-34 (N-phenyl-methanesulfonamide), I-16 ([1,2]thiazinane 1,1-dioxide), I-23 (piperidin-2-one), I-88 (4,4-dimethyl-piperidine-2,6-dione), I-89 (PhNHAc) and I-39 (3,3-diethyl-1H-pyridine-2,4-dione).

EXAMPLE 2

N-[4-tert-Butyl-5-methoxy-2-(2-oxo-1,2-dihydro-pyridin-3-yl)-benzyl]-4-hydroxy-benzamide (I-38)

A-3c $\xrightarrow{\text{step 8}}$

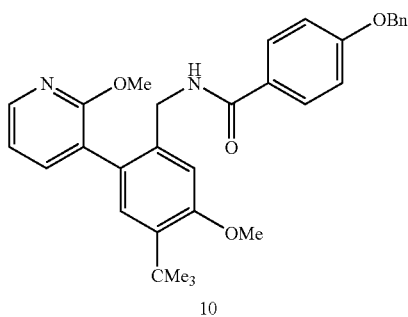

10

$\xrightarrow{\text{step 9}}$ I-38 step 6—A solution of A-3b (0.417 g, 13 mmol, (R'=$R^{2a}$=$R^{2b}$=$R^{2c}$=Me) and sodium azide (0.1 g, 1.56 mmol, 1.2 eq) in DMF (10 mL) was stirred at RT overnight before it was diluted with EtOAc. The organic layer was thrice washed with water, brine, dried (MgSO$_4$), filtered and concentrated to afford 0.425 g (100%) of A-3d.

step 7—A mixture of A-3d (0.425 g, 1.30 mmol) and PPh$_3$ (0.683 g, 2.60 mmol) in THF (10 mL) and water (1 mL) was stirred overnight at RT then poured into water and acidified with 1N aq HCl. The reaction mixture was extracted with a small amount of DCM. The aqueous layer was adjusted to pH 10 with 3N aq NaOH then twice extracted with EtOAc (2×75 mL). The combined EtOAc extracts was washed with brine, dried (MgSO$_4$), filtered and concentrated to afford 0.330 g (85%) of A-3c ($R^a$=$R^b$=H).

step 8—To a solution of A-3c (30 mg, 0.10 mmol), 4-benzyloxybenzoic acid (22.8 mg, 0.10 mmol) in DCM (5 mL) at RT was added HOBt (13.5 mg, 0.10 mmol), EDCI (19.2 mg, 0.10 mmol), Et$_3$N (14 µL, 0.10 mmol). The reaction mixture was stirred overnight at RT then partitioned between EtOAc and water. The organic layer was washed with 1N aq HCl, washed with water, brine, dried (MgSO$_4$), filtered and concentrated. The crude residue was purified on a preparative TLC plate developed with 35% EtOAc/hexanes to afford 0.051 g (100%) of 10.

step 9—A mixture of 10 (21 mg, 0.043 mmol), 48% HBr (0.05 mL) and HOAc (1.5 mL) in a sealed tube was heated at 65° C. for 17 h. The reaction mixture was cooled to RT, carefully poured into saturated aq NaHCO$_3$ and then extracted with EtOAc. The organic layer was washed with brine, dried (MgSO$_4$), filtered and concentrated. The crude residue was purified on a preparative TLC developed with 5% MeOH/DCM to afford 0.015 g (68%) of I-38.

I-36 and I-49 are prepared analogously except in step 8, 4-benzyloxy-benzoic acid is replaced with benzoic acid and nicotinic acid, respectively.

EXAMPLE 3

2-{[4-tert-Butyl-5-methoxy-2-(2-oxo-1,2-dihydro-pyridin-3-yl)-benzyl]-methanesulfonyl-amino}-ethyl acetate (I-30) and N-[4-tert-butyl-5-methoxy-2-(2-oxo-1,2-dihydro-pyridin-3-yl)-benzyl]-N-(2-hydroxy-ethyl)-methanesulfonamide (I-35)

A-3c $\xrightarrow{\text{step 1}}$

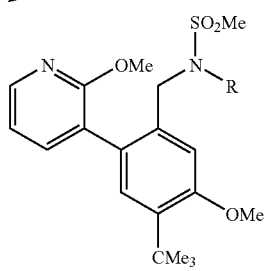

$\xrightarrow{\text{step 3}}$ step 2 $\begin{bmatrix} \text{12a: R = H} \\ \text{12b: R = (CH}_2\text{)}_2\text{OBn} \end{bmatrix}$

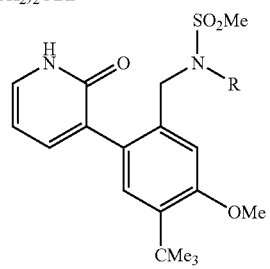

step 4 $\begin{bmatrix} \text{I-30: R = (CH}_2\text{)}_2\text{OAc} \\ \text{I-35: R = (CH}_2\text{)}_2\text{OH} \end{bmatrix}$ step 1—To a solution of A-3c (250 mg, 0.83 mmol) in DCM (5 mL) cooled to 0° C. was added TEA (0.15 mL, 1.08 mmol) followed by a solution of MeSO$_2$Cl (77 µL, 0.99 mmol) in DCM (1 mL). The reaction was stirred at RT for 17 h, diluted with DCM and washed with 1N aq HCl. The organic layer was washed sequentially with water and brine, dried (MgSO$_4$), filtered and concentrated to afford 0.313 g (100%) of 12a.

step 2—To a mixture of 12a (49 mg, 0.13 mmol) in DMF (2 mL) cooled to 0° C. was added NaH (60% in oil dispersion, 6 mg, 0.16 mmol). The reaction mixture was stirred for 30 min then NaI (19 mg, 0.13 mmol) and benzyl 2-bromoethyl ether (35 mg, 0.16 mmol) were added sequentially. The reaction mixture was heated stirred at 65° C. for 3.5 h then cooled to RT, quenched with a saturated aq NH$_4$Cl, and extracted with EtOAc. The organic extract was washed with water, brine, dried (MgSO$_4$), filtered and concentrated. The crude residue was purified on a preparative TLC plate developed with 60% EtOAc/hexane to afford 0.041 g (62%) of 12b.

step 3—A mixture of 12b (41 mg, 0.08 mmol), 48% HBr (0.10 mL) and HOAc (3 mL) in a sealed tube was heated at 65° C. for 17 h. The reaction mixture was cooled to RT, carefully poured into a saturated aq NaHCO$_3$, then extracted with EtOAc. The organic layer was washed with brine, dried (MgSO$_4$), filtered and concentrated. The residue was purified on a preparative TLC plate developed with 7% MeOH/DCM to afford 0.025 g (69%) of I-30.

step 4—A mixture of 12c (21 mg, 0.05 mmol) and 1N aq LiOH (1 mL) in MeOH (1 mL) and THF (1 mL) was stirred overnight at RT then concentrated in vacuo. The residue was taken up in EtOAc, washed sequentially with 1N aq HCl, water and brine, dried ($MgSO_4$), filtered and concentrated to afford 0.019 g (100%) of I-35.

The following are prepared analogously except in step 2, benzyl 2-bromoethyl ether is replaced by the halide in parentheses: I-86 (methyl iodide), I-32 (butyl iodide), I-55 (bromomethyl-cyclopentane, CASRN 3814-30-0), I-26 (benzyl bromide), I-27 (ethyl iodide), I-28 (2-bromopropane)

I-57 is prepared analogously except in step 1, A-3c is replaced with N-[2-(2-benzyloxy-pyridin-3-yl)-4-tert-butyl-5-methoxy-benzyl]-methanesulfonamide, in step 2, benzyl 2-bromoethyl ether is replaced with 4-bromo-piperidine-1-carboxylic acid tert-butyl ester (CASRN 180695-79-8). The benzyloxy moiety is cleaved to afford the corresponding pyridone by catalytic hydrogenolysis according to the procedure in step 4 of example 5 and the Boc group is removed is removed by treating a solution of the pyridone and DCM (5 mL) with a solution of TFA/DCM (1:1, 1 mL).

The following are prepared analogously except in step 1 methanesulfonyl chloride is replaced with the sulfonyl chloride in parentheses and the alkylation in step 2 is omitted: I-19 (4-chlorophenylsulfonyl chloride, CASRN 98-60-2), I-25 (propane-2-sulfonyl chloride, CASRN 10147-37-2), I-20 (phenyl-methanesulfonyl chloride, CASRN 98-09-9), I-87 (2-chlorophenylsulfonyl chloride, CASRN 2905-23-9).

EXAMPLE 4

N-[4-tert-Butyl-5-methoxy-2-(2-oxo-1,2-dihydro-pyridin-3-yl)-benzyl]-N-pyrrolidin-3-ylmethyl-methanesulfonamide (I-31) and N-(1-acetyl-pyrrolidin-3-ylmethyl)-N-[4-tert-butyl-5-methoxy-2-(2-oxo-1,2-dihydro-pyridin-3-yl)-benzyl]-methanesulfonamide (I-48)

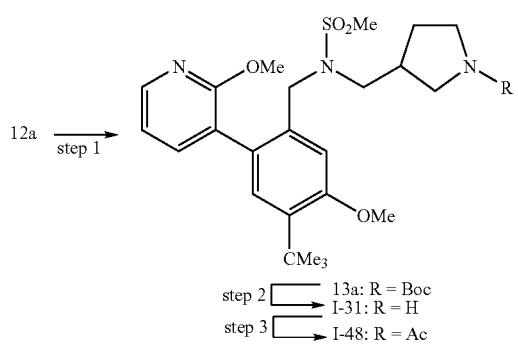

step 1—To a solution of 12a (0.047 g, 0.124 mmol) in DMF (2 mL) was added NaH (6 mg, 0.15 mmol, 60% mineral oil dispersion) and the reaction stirred at RT until gas evolution ceased. To the resulting solution was added sequentially NaI (0.019 g, 0.13 mmol) and tert-butyl 3-bromomethyl-pyrrolidine-1-carboxylate (0.038 g, 0.143 mmol). The reaction mixture was warmed to 65° C. until starting material was consumed. The reaction was cooled to RT and poured into satd aq $NH_4Cl$ and twice extracted with EtOAc. The combined extracts were thrice washed with water, dried ($MgSO_4$), filtered and evaporated. The crude product was purified on a preparative $SiO_2$ TLC developed with EtOAc/hexane to afford 13a.

step 2—A mixture of 13a (46.9 mg), 48% HBr (0.10 mL) and HOAc (3 mL) in a sealed tube was heated at 65° C. for overnight. The reaction mixture was cooled to RT and the volatile solvents were evaporated in vacuo. The residue was taken up in PhMe and re-evaporated. The residue was taken up in water (15 mL) and the pH adjusted to 7 with satd aq $NaHCO_3$. The solution was twice extracted with EtOAc then twice with 15% IPA/DCM. The combined extracts were evaporated and dried under high vacuum for 20 min to afford 21 mg of I-31 as a white solid.

step 3—To a solution of I-31 (0.0152 g, 0.034 mmol), pyridine (6 μL) and DCM (2 mL) was added acetic anhydride (3.7 μL, 0.039 mmol) and the resulting solution stirred overnight at RT. The solution was diluted with EtOAc and washed sequentially with 1M HCl and brine, dried, filtered and evaporated. The crude product was purified on a preparative $SiO_2$ TLC plate developed with 6% MeOH/DCM to afford 11.3 mg of I-48

I-57 is prepared analogously except in step 1 tert-butyl 3-bromomethyl-pyrrolidine-1-carboxylate is replaced with 4-bromo-piperidine-1-carboxylic acid tert-butyl ester (CASRN 180695-79-8) and the Boc group and methyl ether are cleaved according to the procedure in step 3 above.

EXAMPLE 5

3-[5-tert-Butyl-2-(1,1-dioxo-1$\lambda^6$-isothiazolidin-2-ylmethyl)-4-methoxy-phenyl]-1H-pyridin-2-one (I-21)

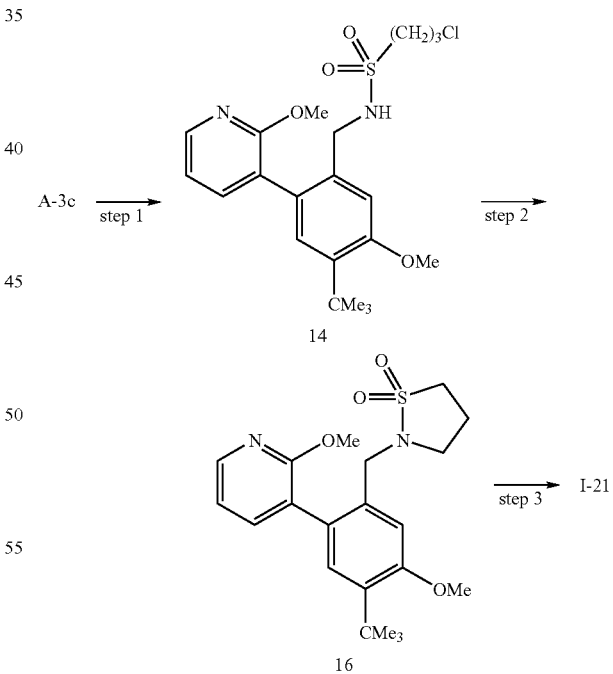

step 1—A mixture of A-3c (81 mg, 0.27 mmol, $R'=R^{2a}=R^{2b}=R^{2c}$=Me, $R^a=R^b$=H), TEA (0.05 mL, 0.34 mmol) and 3-chloropropanesulfonyl chloride (36 μL, 0.297 mmol) in DCM (5 mL) was stirred overnight at RT. The reaction mixture was concentrated in vacuo to afford 14 was used without purification.

step 2—To a solution of 14 in DMF (5 mL) cooled to 0° C. was added NaH (60% in oil dispersion, 32 mg, 0.81 mmol). The reaction mixture was stirred overnight at RT then poured into a saturated aqueous NH₄Cl, and extracted with EtOAc. The combined extracts were washed with water and brine, dried (MgSO₄), filtered and concentrated to afford 16.

step 3—A mixture of 16, 48% HBr (0.20 mL) and HOAc (6 mL) in a sealed tube was heated at 65° C. overnight. The reaction mixture was cooled to RT, carefully poured into a saturated aq. NaHCO₃ and then extracted with EtOAc. The organic layer was washed with brine, dried (MgSO₄), filtered and concentrated. The crude residue was purified on a preparative TLC plate developed with 100% EtOAc to afford 0.028 g, 27% yield over 2 steps) of I-21.

EXAMPLE 6

N-[4-tert-Butyl-5-methoxy-2-(2-oxo-1,2-dihydro-pyridin-3-yl)-benzyl]-sulfamide (I-50)

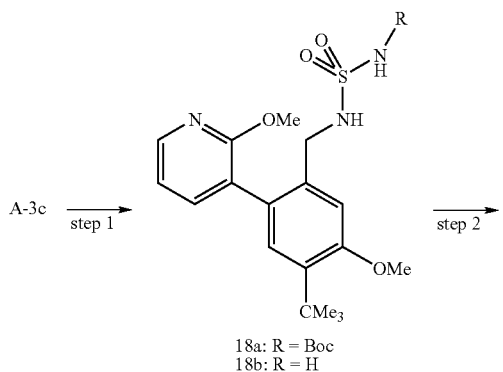

step 1—To a solution of chlorosulfonyl isocyanate (16 mg, 0.011 mmol) in DCM (5 mL) cooled to 0° C. was added a solution of 2-methyl-2-propanol (0.01 mL, 0.011 mmol). The reaction was stirred at 0° C. for 30 min. To the solution was added TEA (0.052 mL, 0.37 mmol) followed by a solution of A-3c (28 mg, 0.093 mmol) in DCM (5 mL). The reaction was warmed up to RT and stirred overnight. The solution was acidified to pH 2-3 with 1N aq HCl and extracted with EtOAc. The organic extract was washed with brine, dried (MgSO₄), filtered and concentrated. The crude residue was purified on a preparative TLC plate developed with 30% EtOAc/hexanes to afford a mixture of 18a (29 mg, 64% yield) and 18b (7 mg, 20% yield).

step 2—A mixture of 18b (7 mg), 48% HBr (25 µL) and HOAc (1 mL) in a sealed tube was heated overnight at 70° C. The reaction mixture was cooled to RT, carefully poured into a saturated aq NaHCO₃ and then extracted with EtOAc. The organic extract was washed with brine, dried (MgSO₄), filtered and concentrated. The crude residue was purified on a preparative TLC developed with 5% MeOH/DCM to afford 3.5 mg of I-50 as a white solid.

EXAMPLE 7

3-[5-tert-Butyl-2-(1,1-dioxo-1$\lambda^6$-[1,2,5]thiadiazolidin-2-ylmethyl)-4-methoxy-phenyl]-1H-pyridin-2-on (I-60)

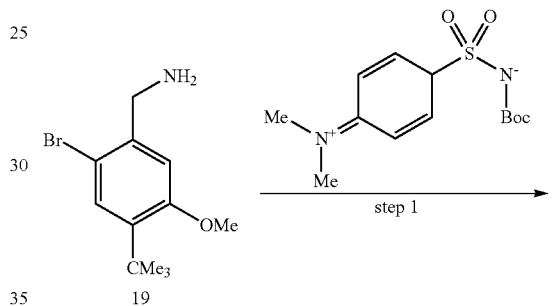

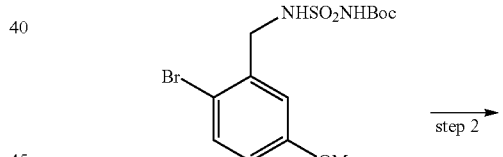

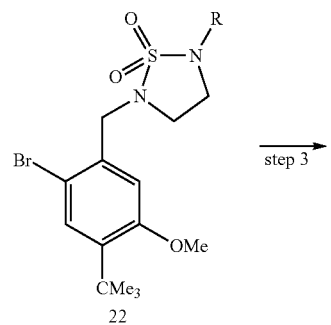

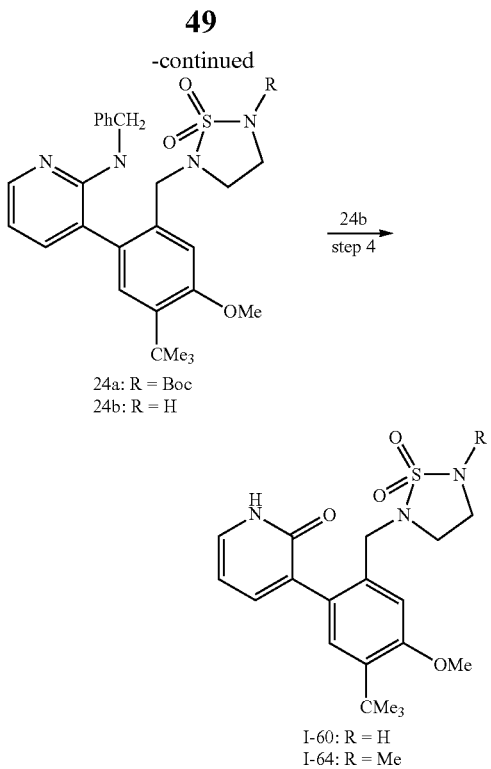

24a: R = Boc
24b: R = H

I-60: R = H
I-64: R = Me step 1—A solution of A-3c (1.00 g, 3.67 mmol) and N-(tert-butylcarbonyl)-N-[4-(dimethylazaniumylidene)-1,4-dihydropyridine-1-yl sulfonyl]azamide (1.11 g, 3.67 mmol) in DCM (25 mL) was stirred overnight at RT. The solvent was removed under reduced pressure. The crude residue was purified by SiO$_2$ chromatography eluting with a EtOAc/hexane gradient (10 to 45% EtOAc) to afford 0.95 g (57%) of 20.

step 2—To a solution of 20 (300 mg, 0.665 mmol) in DMF (10 mL) at room temperature was added NaH (60% in oil dispersion, 67 mg, 1.66 mmol). The reaction was stirred for 30 min then 1,2-dibromoethane (86 µL, 0.99 mmol) was added. The reaction was then heated at 80° C. for 17 h then cooled to RT and quenched with a saturated aq NH$_4$Cl and extracted with EtOAc. The organic extract was washed sequentially with water and brine, dried (MgSO$_4$), filtered and concentrated. The crude product was purified on a preparative TLC plate developed with 30% EtOAc/hexane to afford 0.104 g (33%) of 22a.

step 3—A sealed tube containing 22 (104 mg, 0.22 mmol), 2-benzoxy-3-pyridine boronic acid (75 mg, 0.33 mmol), Na$_2$CO$_3$ (70 mg, 0.66 mmol) and Pd(PPh$_3$)$_4$ (25 mg, 0.022 mmol) in a mixture of MeOH (3 mL) and DCM (1 mL) was irradiated in a microwave synthesizer at 120° C. for 30 min. The reaction was diluted with DCM and filtered through a plug of CELITE and the filtrate was concentrated. The crude residue was purified on a preparative TLC plate developed with 40% EtOAc/hexane to afford 23 mg (20%) of 24a (26 mg, 20% yield) and 65 mg (61%) of 24b.

step 4—A mixture of 24b (38 mg, 0.08 mmol) and 10% Pd/C (10 mg) in MeOH (10 mL) under 1 atmosphere of H$_2$ at RT was stirred for 1 h. The catalyst was filtered off and the filtrate was concentrated. The crude residue was purified on a preparative TLC plate developed with 6% MeOH/DCM to afford 0.021 g (69%) of I-60 as a white solid.

EXAMPLE 8

3-[5-tert-Butyl-4-methoxy-2-(5-methyl-1,1-dioxo-1λ$^6$-[1,2,5]thiadiazolidin-2-ylmethyl)-phenyl]-1H-pyridin-2-one (I-64)

step 1—To a solution of 24b (24 mg, 0.05 mmol) in DMF (2 mL) at RT was added NaH (60% in oil dispersion, 3 mg, 0.075 mmol). The reaction mixture was stirred for 30 minutes then MeI (4 µL, 0.065 mmol) was added. The reaction mixture was allowed to stir overnight at RT then poured into a saturated aqueous NH$_4$Cl and extracted with EtOAc. The organic extract was washed with water, brine, (MgSO$_4$), filtered and concentrated to afford 24c.

step 2—A suspension of 24c from step 1 and 10% Pd/C (10 mg) in MeOH (15 mL) under 1 atmosphere of H$_2$ at RT was stirred for 1 h. The catalyst was filtered off and the filtrate was concentrated. The crude residue was purified on a preparative TLC plate developed with EtOAc to afford 15.6 mg (77% over two steps) of I-64 as a white solid.

EXAMPLE 9

3-[5-tert-Butyl-4-methoxy-2-(2-oxo-pyrrolidin-1-ylmethyl)-phenyl]-1H-pyridin-2-one (I-18)

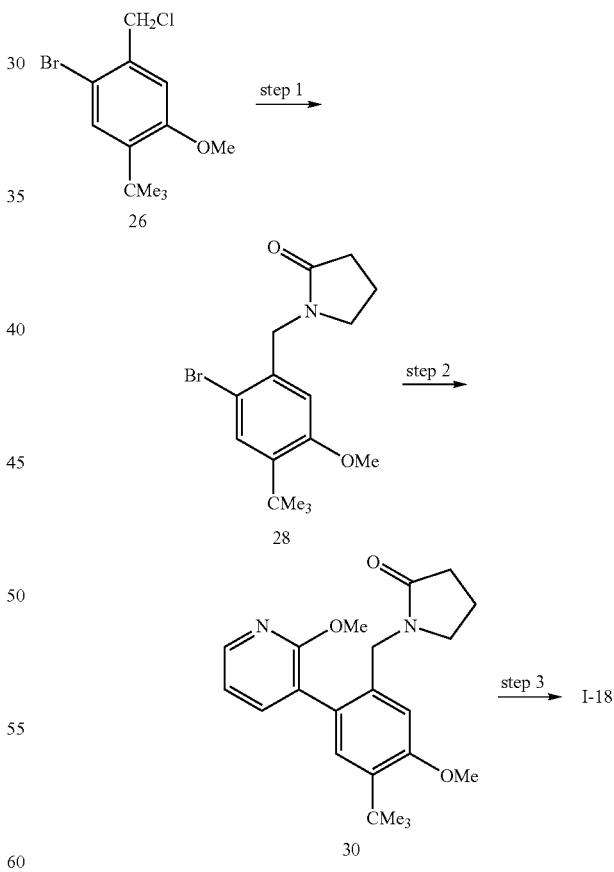

Preparation of 26—To a solution of 4-tert-butyl-3-methoxy-benzoic acid (3 g, 14.4 mmol, CASRN 79822-46-1) and THF (60 mL) cooled to 0° C. was added a solution of LiAlH$_4$ in THF (29 mL, 28.8 mmol, 1M THF solution). The reaction was stirred overnight at RT then quenched by dropwise addition of aqueous THF (1.1 mL of water in 10 mL of THF) followed by 1.1 mL of 15% NaOH and then 3.3 mL of water.

The reaction was stirred for 1 h then solid Na₂SO₄ was added and the resulting suspension stirred overnight, filtered through a pad of CELITE, and evaporated to afford 2.8 g of 4-tert-butyl-3-methoxy-benzyl alcohol.

A solution of the alcohol (2.08 g, 10.72 mmol) and CCl₄ (75 mL) NBS (2.1 g, 11.8 mmol) was stirred for 15 min then poured into a mixture of ice and NaHSO₃, extracted with DCM and the organic extract washed with brine. The solution was evaporated, taken up in hexane (80 mL) and MgSO₄ was added. The solid was filtered and the filtrate evaporated to afford 2.9 g (100%) of 2-bromo-4-tert-butyl-5-methoxy-benzyl alcohol (25).

The resulting alcohol (2.0 g, 7.3 mmol) was dissolved in CHCl₃ (50 mL) and SOCl₂ (7 mL, 9.5 mmol) was added and the resulting solution was stirred for 1 h at RT then at 40° C. for 30 min. The solution was concentrated to afford 2 g of 2-bromo-4-tert-butyl-5-methoxy-benzyl chloride.

step 1—To a solution of pyrrolidin-2-one (34 mg) in DMF (5 mL) at RT was added NaH (60% in oil dispersion, 14 mg). The reaction was stirred for 20 min then 100 mg of 2-bromo-4-tert-butyl-5-methoxybenzyl chloride (prepared from A-1b as described in step 3 of example 1) was added. The reaction mixture was stirred for 3 d then partitioned between water and EtOAc. The organic layer was washed sequentially with water and brine, dried (Na₂SO₄), filtered and concentrated. The crude residue was purified on a preparative TLC plate developed with 35% EtOAc/hexanes to afford 100 mg of 28 as a colorless oil.

step 2—A sealed tube containing 28 (100 mg), 2-methoxy-3-pyridine boronic acid (65 mg), Na₂CO₃ (78 g) and Pd(PPh₃)₄ (34 mg) in a mixture of MeOH (4 mL) and DCM (1 mL) was irradiated in a microwave synthesizer at 115° C. for 20 min. The organic volatiles were removed under reduced pressure. The residue was partitioned between EtOAc and water. The organic layer was washed with brine, dried (Na₂SO₄), filtered and concentrated. The crude residue was purified on a preparative TLC plate developed with 7% MeOH/DCM to afford 70 mg of 30 as a yellow oil.

step 3—A mixture of 30 (70 mg), 48% HBr (105 µL) and HOAc (3 mL) in a sealed tube was heated overnight at 70° C. The reaction mixture was cooled to RT, carefully poured into a saturated aq NaHCO₃ and extracted with EtOAc. The organic layer was washed with brine, dried (Na₂SO₄), filtered and concentrated. The crude residue was purified on a preparative TLC plate developed with 5% MeOH/DCM to afford 40 mg of I-18 as a white solid.

EXAMPLE 10

N-{1-[4-tert-Butyl-5-methoxy-2-(2-oxo-1,2-dihydro-pyridin-3-yl)-phenyl]-ethyl}-N-methyl-methane-sulfonamide (I-53) and N-{1-[4-tert-butyl-5-methoxy-2-(2-oxo-1,2-dihydro-pyridin-3-yl)-phenyl]-ethyl}-methanesulfonamide (I-52)

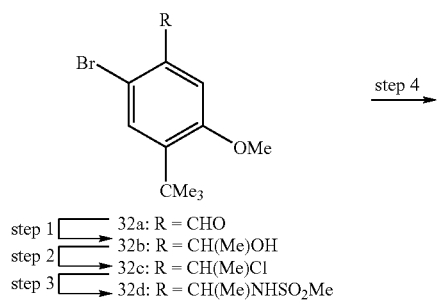

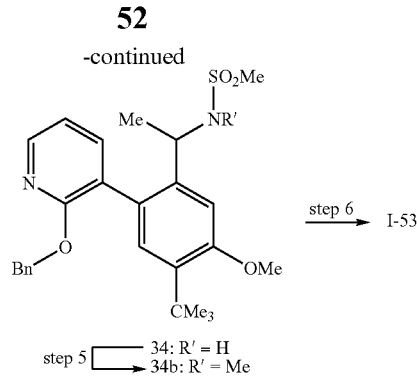

step 1—To a solution of 32a (1.00 g, 3.70 mmol) in THF (15 mL) cooled to 0° C. was added dropwise a solution of MeMgCl (3.0M in THF, 1.48 mL, 4.44 mmol). The reaction mixture was stirred at 0° C. for 15 min then quenched with a saturated aq NH₄Cl and extracted with ether. The organic layer was washed with brine, dried (MgSO₄), filtered and concentrated to afford 0.97 g of 32b as a white solid.

step 2—To a solution of the 32b (1.00 g, 4.80 mmol) in DCE (30 mL) cooled 0° C. was added dropwise a solution of SOCl₂ (1.05 mL, 4.4 mmol). The reaction was stirred overnight at RT before the organic volatiles were removed under reduced pressure. The residue was dissolved in DCM, washed with brine, dried (MgSO₄) and filtered over a short plug of SiO₂. The filtrate was concentrated in vacuo to afford 0.98 g (90%) of 32c.

step 3—To a solution of methanesulfonamide (0.10 g, 1.08 mmol) in DMF (5 mL) cooled to 0° C. was added NaH (60% in oil dispersion, 52 mg, 1.30 mmol). The reaction was stirred at 0° C. for 20 min then a solution of 32c and DMF (2 mL) was added dropwise. This reaction was heated at 80° C. for 17 h, then cooled to RT, poured into a saturated aq NH₄Cl and extracted with EtOAc. The organic extract was washed sequentially with water and brine, dried (MgSO₄), filtered and concentrated. The crude residue was purified by SiO₂ chromatography eluting with a EtOAc/hexane gradient (20 to 60% EtOAc) to afford 0.193 g (55%) of 32d.

step 4—A sealed tube containing 32d (100 mg, 0.14 mmol), 2-benzoxy-3-pyridine boronic acid (63 mg, 0.28 mmol), Na₂CO₃ (44 mg, 0.42 mmol) and Pd(PPh₃)₄ (16 mg, 0.014 mmol) in a mixture of MeOH (3 mL) and CH₂Cl₂ (1 mL) was irradiated in a microwave synthesizer at 125° C. for 30 min. The reaction mixture was diluted with DCM, filtered through a pad of CELITE, and the filtrate was concentrated. The crude residue was purified on a preparative TLC plate developed with 30% EtOAc/hexanes to afford 0.039 g (60%) of 34a.

step 5—To a solution of 34a (19 mg, 0.04 mmol) in DMF (1.5 mL) cooled to 0° C. was added NaH (60% in oil dispersion, 2.4 mg, 0.06 mmol). The reaction was stirred at 0° C. for 20 min then MeI (4 µL, 0.06 mmol) was added. The reaction mixture was stirred overnight at RT then quenched with satd aq NH₄Cl, and extracted with EtOAc. The organic extract was washed sequentially with water and brine, dried (MgSO₄), filtered and concentrated to afford 0.019 g (97%) of 34b.

step 6—A mixture of 34b and 10% Pd/C (10 mg) in MeOH (10 mL) under 1 atmosphere of H₂ at RT was stirred for 1 h. The catalyst was filtered and the filtrate was concentrated. The crude residue was passed through a short plug of SiO₂ and the resulting solution was concentrated in vacuo to afford 0.016 g (96%) of I-53 as a white solid.

I-52 was prepared analogously except step 5 was omitted.

EXAMPLE 11

4-Amino-N-[4-tert-butyl-5-methoxy-2-(2-oxo-1,2-dihydro-pyridin-3-yl)-benzyl]-benzamide (I-42) and N-[4-tert-butyl-5-methoxy-2-(2-oxo-1,2-dihydro-pyridin-3-yl)-benzyl]-4-methanesulfonylamino-benzamide (I-43)

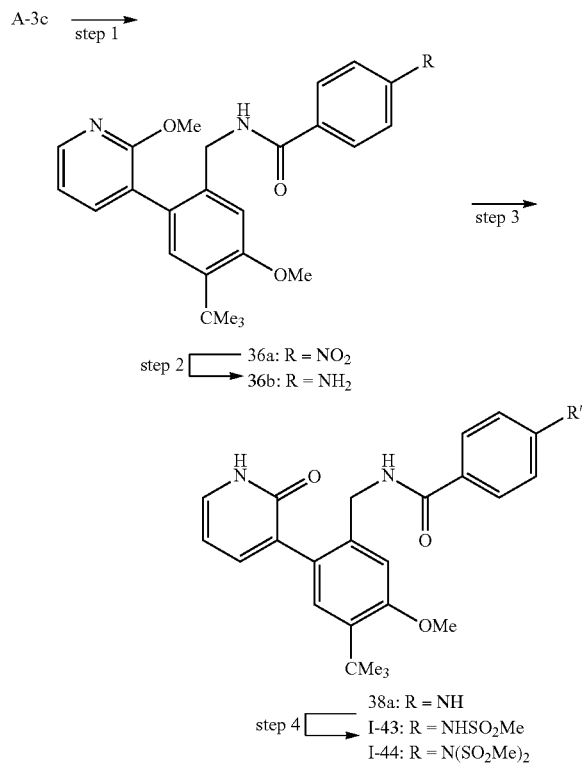

step 1—To a solution of A-3c (0.03 g, 0.1 mmol, R'=R$^{2a}$=R$^{2b}$=R$^{2c}$=Me) in DCM (5 mL) was added sequentially TEA (0.02 mL, 0.15 mmol) and p-nitro-benzoyl chloride. The reaction was stirred at RT overnight then partitioned between EtOAc and 1M HCl. The EtOAc extract was washed with brine, dried (MgSO$_4$) filtered and evaporated. The residue was purified on a SiO$_2$ preparative TLC plate developed with 30% EtOAc/hexane to afford 43.2 mg (96%) of 36a.

step 2—To a solution of 36a in EtOAc and DMF (2 mL of 1:1 solution) was added SnCl$_2$.2H$_2$O and the resulting mixture stirred overnight. The reaction mixture was poured into satd aq NaHCO$_3$ and twice extracted with EtOAc. The combined extracts were thrice washed with water then with brine, dried (MgSO$_4$), filtered and evaporated to afford 39 mg (97%) of 36b.

step 3—The pyridinyl ether was converted to 38a in accord with the procedure in step 5 of example 1.

step 4—Sulfonylation of 38a in accord with the procedure in step 1 of example 3 afford a separable mixture contain I-43 and I-44.

I-63 can be prepared analogously except in step 1, 4-nitro-benzoyl chloride is replaced with 3-nitro-benzoyl chloride.

EXAMPLE 12

N-[4-tert-Butyl-5-methoxy-2-(2-oxo-1,2-dihydro-pyridin-3-yl)-benzyl]-methane sulfonamide (I-13)

step 1—To a solution of B-1a (3 g, 14.4 mmol, R$^{2a}$=R$^{2b}$=R$^{2c}$=Me) in DCM cooled to 5° C. was added a drop of DMF followed by dropwise addition of oxalyl chloride (2.74 g, 21.0 mmol). The resulting solution was stirred at RT for 32 h then heated to 40° C. for 3 h. The reaction mixture was cooled and concentrated in vacuo. The residue was dissolved in DCM and added with stirring to concentrated aq NH$_4$OH (10 mL) which was cooled to 0° C. The volatile solvents were removed in vacuo and the residual solid was filtered, washed with water and dried to afford 2.8 g of B-1b as a white solid.

step 2—To a solution of LiAlH$_4$ (14.2 mL of a 1M THF solution) was added a hot solution of B-1b (1.4 g, 7.1 mmol) dissolved in THF (60 mL). (The solution had to be heated to dissolve the amide.) The solution was heated at reflux for 24 h, cooled to 5° C. and a solution containing water (0.54 mL) and THF (20 mL) was added to quench the reaction followed sequential addition of 15% aq NaOH (0.54 mL) and water (1.62 mL). The resulting mixture was stirred for 1 h and filtered through CELITE. The CELITE was rinsed with EtOAc. The resulting solution was filtered dried and concentrated in vacuo to afford B-2a in quantitative yield.

step 3—To a solution of B-2a (0.15 g, 0.78 mmol) in DCM 10 mL) cooled to 5° C. was added sequentially TEA (0.135 mL, 0.98 mmol) and methanesulfonyl chloride (0.103 g, 0.90 mmol). The resulting solution was stirred at RT overnight, poured into a mixture of ice and 1 M HCl and the resulting mixture twice extracted with EtOAc. The combined extracts were dried (MgSO$_4$), filtered and evaporated. The crude product was purified on two SiO$_2$ preparative TLC plates developed with 50% EtOAc/hexane to afford 0.169 g of B-2b as a white solid.

step 4—To a solution of B-2b (0.169 g, 0.624 mmol) in DMF cooled to 5° C. was added NBS (0.17 g, 0.94 mmol). The solution was stirred overnight at RT, then partitioned between EtOAc and aq NH$_4$Cl. The EtOAc was thrice washed with water, dried (MgSO$_4$), filtered and evaporated. The crude product was purified by SiO$_2$ chromatography eluting with a EtOAc/hexane gradient (5 to 30% EtOAc) to afford 0.1 g of B-3 as a white solid.

The preparation of I-13 is completed by Suzuki coupling of B-3 and 2-methoxy-pyridin-3-yl boronic acid as described in step 2 of example 1 and cleavage of the methoxy-pyridinyl ether as described in step 5 of example 1.

The following are prepared by sulfonylation or acetylation of B-2a as described in step 3 except methanesulfonyl chloride was replaced with the reagent in parentheses: I-12 (acetic anhydride), I-24 (ethanesulfonyl chloride). I-45 is prepared by sulfonylation of B-2a with methanesulfonyl chloride and coupling the resulting sulfonamide with 5-fluoro-2-methoxypyridin-3-yl boronic acid (CASRN 957120-32-0) in place of 2-methoxypyridin-3-yl boronic acid.

EXAMPLE 13

N-[4-tert-Butyl-5-methoxy-2-(2-oxo-1,2-dihydro-pyridin-3-yl)-benzyl]-3-methanesulfonylamino-N-methyl-benzamide (I-65)

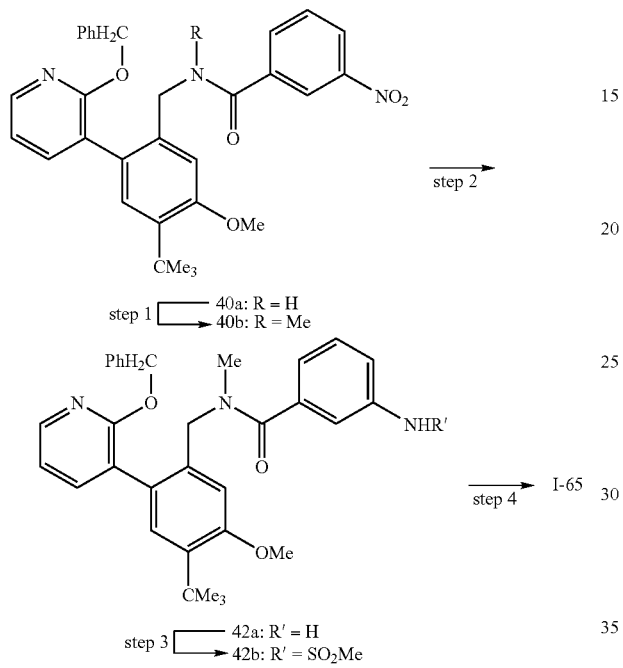

step 1—To a solution of 40a (0.19 g, 0.36 mmol) in DMF (5 mL) at RT was added NaH (29 mg, 0.72 mmol, 60% in oil dispersion). The reaction mixture was stirred at RT for 20 min then MeI (50 µL, 0.72 mmol) was added. The reaction was stirred overnight at RT then poured into a saturated aq NH₄Cl and extracted with EtOAc. The organic extract was washed sequentially with water, brine, dried (MgSO₄), filtered and concentrated to afford 0.194 g (100%) of 40b.

step 2—A mixture of 40b (194 mg, 0.36 mmol) and SnCl₂·2H₂O (450 mg, 2.00 mmol) in EtOH (5 mL) and DMF (5 mL) was stirred overnight at RT. The reaction was poured into a mixture of saturated aq NaHCO₃ and EtOAc. The reaction mixture was passed through a plug of CELITE. The organic layer was separated, washed sequentially with water and brine, dried (MgSO₄) and concentrated to afford 0.180 g (100%) of 42a.

step 3—To a solution of 42a (59 mg, 0.116 mmol) in DCM (5 mL) cooled to 0° C. was added sequentially pyridine (0.30 mL) and a solution of MeSO₂Cl (10 µL, 0.133 mmol) in DCM (2 mL). The reaction was warmed to RT and stirred overnight. The reaction was diluted with 1N aq HCl solution and extracted with EtOAc. The organic extract was washed with brine, dried (MgSO₄), filtered and concentrated. The crude residue was purified on a preparative SiO₂ TLC plate developed with 80% EtOAc/hexanes to afford 0.049 g (72%) of 42b.

step 4—A suspension of 42b (49 mg, 0.083 mmol) and 10% Pd/C (15 mg) in MeOH (10 mL) at RT under 1 atmosphere of H₂ was stirred for 1 h. The catalyst was filtered off and the filtrate was concentrated. The crude residue was purified on a preparative SiO₂ TLC developed with 5% MeOH/DCM to afford 27 mg (66%) of I-65 as a white solid.

EXAMPLE 14

4-tert-Butyl-5-methoxy-2-(2-oxo-1,2-dihydro-pyridin-3-yl)-benzoic acid (I-4) and 3-(5-tert-Butyl-2-hydroxymethyl-4-methoxy-phenyl)-1H-pyridin-2-one (I-2)

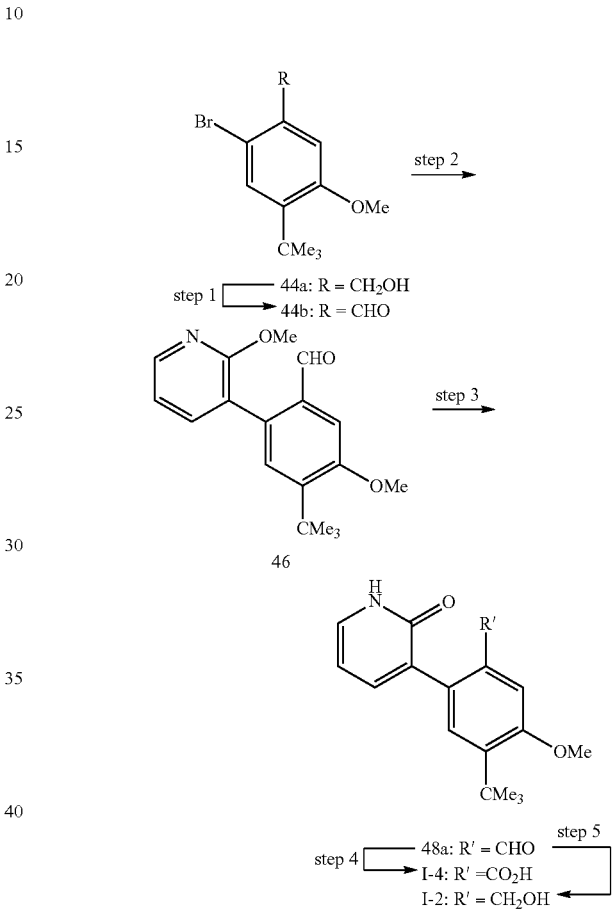

step 1—A mixture of 44a (10.00 g) and MnO₂ (25.46 g) in DCM (400 mL) was stirred for 3 d at RT then the solid was filtered off. The filtrate was concentrated to afford 8.98 g of 44b as a white solid.

step 2—A sealed tube containing 44b (100 mg), 2-methoxy-3-pyridine boronic acid (85 mg), Na₂CO₃ (59 g) and Pd(dppf)Cl₂ (19 mg) in a mixture of MeOH (4 mL), water (1 mL) and DCM (1 mL) was irradiated in a microwave synthesizer at 115° C. for 20 min. The organic volatiles were removed under reduced pressure. The residue was partitioned between EtOAc and water. The organic layer was washed with brine, dried (Na₂SO₄), filtered and concentrated. The crude residue was purified on a preparative SiO₂ TLC plate to afford 124 mg of 46.

step 3—A mixture of 46 (124 mg), 48% HBr (0.30 mL) and HOAc (2 mL) in a sealed tube was heated at 70° C. for 7 h. The reaction mixture was cooled to RT, carefully poured into a saturated aq. NaHCO₃, and extracted with EtOAc. The organic layer was washed with brine, dried (MgSO₄) and concentrated. The crude residue was purified by SiO₂ chromatography eluting with a EtOAc/hexane gradient (50 to 100% EtOAc) to afford 103 mg of 48a as a white solid.

step 4—To a solution 48a (40 mg) in a mixture of tert-BuOH (4 mL) and water (4 mL) cooled to 0° C. was added 2-methyl-2-butene (1 mL), $NaH_2PO_4 \cdot H_2O$ (193 mg), and $NaClO_2$ (38 mg). The reaction was stirred at 0° C. for 2.5 h. The reaction was quenched with dilute aq $Na_2SO_3$ solution then extracted with EtOAc. The organic layer was washed with brine, dried ($MgSO_4$), filtered and concentrated. The crude residue was purified by $SiO_2$ chromatography eluting with a MeOH/DCM gradient (10 to 20% MeOH) to afford 17 mg of I-4 as a white solid.

step 5—To a solution of 48a (60 mg) in a mixture of THF (3 mL) and EtOH (2 mL) cooled to 0° C. was added $LiBH_4$ (21 mg). The reaction was stirred at 0° C. for 30 min then the organic volatiles were removed under reduced pressure. The residue was partitioned between EtOAc and water. The organic layer was washed with brine, dried ($MgSO_4$), filtered and concentrated. The crude residue was purified by $SiO_2$ chromatography eluting with a EtOAc/hexane gradient (50 to 100% EtOAc) to afford 48 mg of I-2 which was recrystallized from a mixture of EtOAc/hexanes.

EXAMPLE 15

3-[4-tert-Butyl-5-methoxy-2-(2-oxo-1,2-dihydro-pyridin-3-yl)-phenyl]-propionic acid methyl ester (I-3)

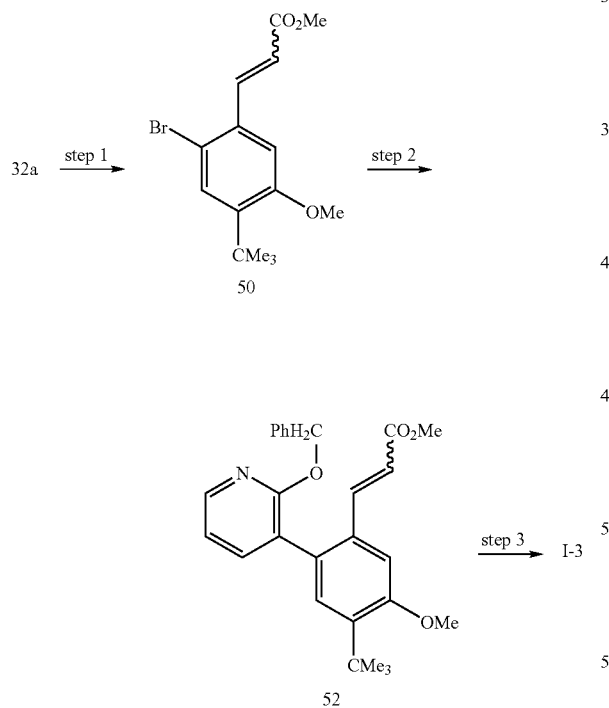

step 1—To a solution of methyl triphenylphosphonoacetate (0.622 µL) in THF (10 mL) cooled to 0° C. was added a solution of NaHMDS (1.0M in THF, 3.84 mL). The resulting mixture was stirred at 0° C. for 15 min then a solution of 32a (0.70 g) in THF (4 mL) was added. The reaction mixture was stirred and warmed to RT over a 2 h period. The reaction was quenched with 1N aq HCl and diluted with ether. The organic layer was washed with brine, dried ($MgSO_4$) and concentrated. The crude residue was purified by $SiO_2$ chromatography eluting with a EtOAc/hexane gradient (5 to 15%) to afford 374 mg of 50 as a mixture of E and Z isomers.

step 2—Suzuki condensation of 50 and 2-benzyloxy-pyridin-3-yl boronic acid is carried out as described in step 4 of example 10 to afford 52.

step 3—A mixture of 52 (65 mg) and 20% $Pd(OH)_2$/C (100 mg) in EtOAc (15 mL) at RT was stirred under 1 atmosphere of $H_2$ for 1 h before the catalyst was filtered off. The filtrate was concentrated and the crude residue was purified by $SiO_2$ chromatography eluting with a EtOAc/hexane gradient (50 to 100% EtOAc) to afford 43 mg of I-3 as a syrup which solidified upon standing.

3-[4-tert-Butyl-5-methoxy-2-(2-oxo-1,2-dihydro-pyridin-3-yl)-phenyl]-propionic acid (I-1) was prepared analogously except 2-methoxy-pyridin-3-yl boronic acid was used in place of 2-benzyloxy-pyridin-3-ylboronic acid in step 3 and hydrolysis of the ester occurred concomitantly with HBr/HOAc mediated cleavage of the pyridinyl ether.

EXAMPLE 16

[4-tert-Butyl-5-methoxy-2-(2-oxo-1,2-dihydro-pyridin-3-yl)-phenyl]-acetic acid (I-7)

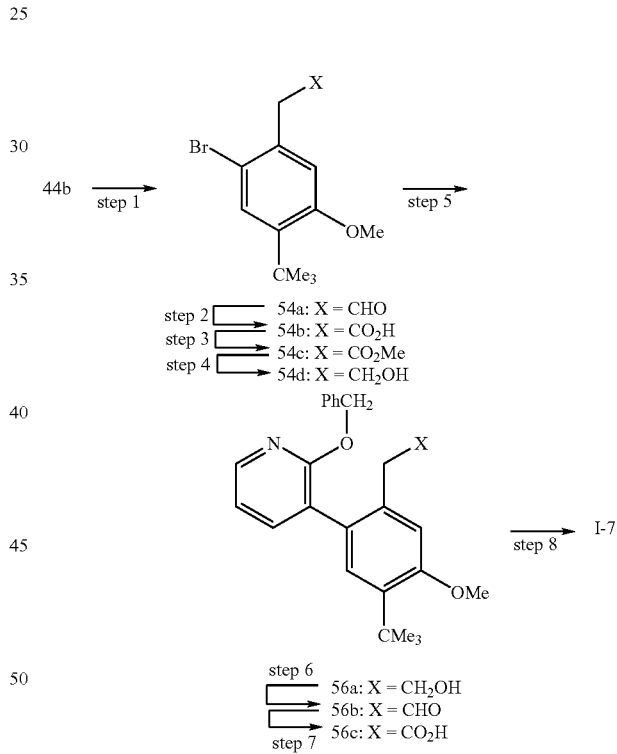

step 1—To a solution of methoxymethyl triphenylphosphonium chloride (17.00 g) in THF (25 mL) cooed to 0° C. was added a solution of NaHMDS (1.0M in THF, 50 mL). The resulting mixture was stirred at 0° C. for 20 min then a solution of 44b (1.35 g) in THF (5 mL) was added. The reaction mixture was stirred and warmed from 0° C. to RT overnight then quenched with a saturated aq $NH_4Cl$ and extracted with EtOAc. The organic layer was washed with brine, dried ($Na_2SO_4$), filtered and concentrated. The crude residue was purified by $SiO_2$ chromatography eluting with a EtOAc/hexane gradient (5 to 10% EtOAc) to afford 2.10 g of a colorless oil which was dissolved in a mixture of acetone (150 mL) and water (3 mL) containing TsOH (0.5 g) and heated at reflux for 3 h before the organic volatiles were removed. The residue was partitioned between EtOAc and water and the organic layer washed with brine, dried (Na$_2$SO$_4$), filtered and concentrated. The crude residue was purified by SiO$_2$ chromatography eluting with a EtOAc/hexane gradient (5 to 20% EtOAc) to afford 1.0 g of 54a as a colorless oil.

step 2—To a solution of 54a (400 mg) in a mixture of tert-BuOH (20 mL) and water (20 mL) was added 2-methyl-2-butene (3 mL), NaH$_2$PO$_4$.H$_2$O (2.30 g) and NaClO$_2$ (634 mg). The reaction was stirred at 0° C. for 1.5 h then a dilute aq HCl solution was added and the reaction mixture was extracted with EtOAc. The organic layer was washed with brine, dried (Na$_2$SO$_4$), filtered and concentrated to afford 450 mg of 54b as a solid.

step 3—A solution of 54b (200 mg) in a mixture of concentrated H$_2$SO$_4$ (15 drops) and MeOH (25 mL) was heated at reflux overnight. The solvent was removed under reduced pressure. The residue was purified on a SiO$_2$ preparative TLC plate developed with 25% EtOAc/hexanes to afford 110 mg of 54c.

step 4—To a solution of 54c (110 mg) in THF (5 mL) cooled to 0° C. was added a solution of LiAlH$_4$ (1.0M in THF, 0.70 mL). The reaction was stirred at 0° C. for 30 min then quenched with water and then extracted with EtOAc. The organic layer was washed with brine, dried (Na$_2$SO$_4$), filtered and concentrated. The crude residue was purified on a preparative SiO$_2$ TLC plate developed with 35% EtOAc/hexanes to afford 65 mg of 54d as a colorless oil.

step 5—Suzuki condensation of 54d and 2-benzyloxy-pyridin-3-yl boronic acid is carried out as described in step 4 of example 10. The crude residue was purified by preparative SiO$_2$ TLC plate developed with 30% EtOAc/hexanes to afford 90 mg of 56a as a colorless oil.

step 6—To a solution of 56a (90 mg) in DCM (5 mL) cooled to 0° C. was added Na$_2$CO$_3$ (73 mg) followed by the Dess-Martin periodinate (195 mg) in three portions. The reaction was stirred at 0° C. for 1 h. The reaction was diluted with water and extracted with DCM. The organic layer was washed with brine, dried (Na$_2$SO$_4$), filtered and concentrated. The crude residue was purified on a SiO$_2$ preparative TLC plate developed with 15% EtOAc/hexanes to afford 60 mg of 56b as a colorless oil.

step 7—To a solution of 56b (60 mg) in a mixture of tert-BuOH (5 mL) and water (5 mL) was added 2-methyl-2-butene (327 µL), NaH$_2$PO$_4$.H$_2$O (256 mg), and NaClO$_2$ (42 mg). The reaction was stirred and warmed from 0° C. to RT over a period of 1.5 h then extracted with EtOAc. The organic layer was washed with brine, dried (Na$_2$SO$_4$), filtered and concentrated. The crude residue was purified on a preparative SiO$_2$ TLC plate developed with 5% MeOH/DCM to afford 65 mg of 56c as a white solid.

step 8—A mixture of 56c (65 mg) and 10% Pd/C (10 mg) in MeOH (5 mL) was stirred under 1 atmosphere of H$_2$ for 1 h. The catalyst was filtered off, and the filtrate was concentrated. The crude residue was purified on a preparative SiO$_2$ TLC plate developed with 10% MeOH/DCM to afford 25 mg of I-7 as a white solid.

3-[5-tert-Butyl-2-(2-hydroxy-ethyl)-4-methoxy-phenyl]-1H-pyridin-2-one (I-5) is prepared by Suzuki coupling of 54d and 2-benzyloxy-3-(4,4,5,5-tetramethyl-[1,3,2]dioxaborolan-2-yl)-pyridine followed by catalytic hydrogenolysis to cleave the benzyl ether. I-5 is converted to 3-[2-(2-amino-ethyl)-5-tert-butyl-4-methoxy-phenyl]-1H-pyridin-2-one by displacement of the alcohol with CBr$_4$/PPh3 as in step 1 of example 25, displacement of the bromide with azide and reduction with PPh$_3$ as in steps 6 and 7 of example 2. Sulfonylation of the amine with methanesulfonyl chloride then affords N-{2-[4-tert-butyl-5-methoxy-2-(2-oxo-1,2-dihydro-pyridin-3-yl)-phenyl]-ethyl}-methanesulfonamide (I-17).

EXAMPLE 17

2-[4-tert-Butyl-5-methoxy-2-(2-oxo-1,2-dihydro-pyridin-3-yl)-phenyl]-N-methyl-acetamide (I-10)

step 1—To a solution of 56c (95 mg) in DMF (5 mL) cooled to 0° C. was added MeNH$_2$ (2.0M in THF, 234 µL), HOBt (63 mg) and EDCI (90 mg). The reaction mixture was stirred overnight at RT then diluted with water and extracted with EtOAc. The organic extract was washed sequentially with water and brine, dried (Na$_2$SO$_4$), filtered and concentrated. The crude residue was purified on a preparative SiO$_2$ TLC plate developed with 7% MeOH/DCM to afford 55 mg of 2-[2-(2-benzyloxy-pyridin-3-yl)-4-tert-butyl-5-methoxy-phenyl]-N-methyl-acetamide (57) as a colorless oil.

step 2—A mixture of 57 (55 mg) and 10% Pd/C (10 mg) in MeOH (5 mL) at RT was stirred under 1 atmosphere of H$_2$ for 0.5 h. The catalyst was filtered off and the filtrate was concentrated. The crude residue was purified on a preparative SiO$_2$ TLC developed with 10% MeOH/DCM to afford 45 mg of I-10 as a white solid.

EXAMPLE 18

2-[4-tert-Butyl-5-methoxy-2-(2-oxo-1,2-dihydro-pyridin-3-yl)-phenyl]-acetamide (I-11)

To a solution of 56c (50 mg) in DCM (3 mL) was added DMF (2 drops) and followed by oxalyl chloride (27 µL). The reaction mixture was heated at reflux for 2 h then concentrated in vacuo. The residue was taken up in THF (3 mL) and NH$_4$OH (10 drops) was added at RT. The reaction mixture was stirred for 1 h before the organic volatiles were removed under reduced pressure. The crude residue was purified on a preparative SiO$_2$ TLC plate developed with 15% MeOH/DCM to afford 20 mg of 2-[2-(2-benzyloxy-pyridin-3-yl)-4-tert-butyl-5-methoxy-phenyl]-acetamide.

Cleavage of the benzyl ether to afford I-11 is carried out by catalytic hydrogenolysis as described in step 2 of example 17.

EXAMPLE 19

4-tert-Butyl-5-methoxy-N-methyl-2-(2-oxo-1,2-dihydro-pyridin-3-yl)-benzamide (I-9)

2-Bromo-4-tert-butyl-5-methoxybenzoic acid (58) can be prepared by oxidation of 44a or 44b step 1—To a solution of 58 (150 mg) in DMF (10 mL) cooled to 0° C. was added MeNH$_2$ (0.52 mL, 2.0 M in THF,), HOBt (140 mg) and EDCI (200 mg). The reaction mixture was then stirred overnight at RT then diluted with 1N aq HCl solution and extracted with EtOAc. The organic layer was washed sequentially with water and brine, dried (Na$_2$SO$_4$), filtered and concentrated. The crude residue was purified by SiO$_2$ chromatography eluting with a MeOH/DCM gradient (0 to 10% MeOH) to afford 140 mg of 2-bromo-4-tert-butyl-5-methoxy-N-methyl-benzamide (60) as a white solid.

step 2—A sealed tube containing 60 (70 mg), 2-benzoxy-3-(4,4,5,5-tetramethyl-[1,3,2]dioxaborolan-2-yl)-pyridine (145 mg), Na$_2$CO$_3$ (62 g) and Pd(PPh$_3$)$_4$ (27 mg) in a mixture of MeOH (4 mL) and DCM (1 mL) was irradiated in a microwave synthesizer at 115° C. for 30 min. The organic volatiles were removed under reduced pressure and the residue was partitioned between EtOAc and water. The organic layer was washed with brine, dried ($Na_2SO_4$), filtered and concentrated. The crude residue was purified on a preparative $SiO_2$ TLC plate developed with 40% EtOAc/hexanes to afford 95 mg of 2-(2-benzyloxy-pyridin-3-yl)-4-tert-butyl-5-methoxy-N-methyl-benzamide (62) as a colorless oil.

step 3—A mixture of 62 (95 mg) and 10% Pd/C (10 mg) in MeOH (5 mL) at RT was stirred under 1 atmosphere of $H_2$ for 0.5 h. The catalyst was filtered off, and the filtrate was concentrated. The crude residue was purified on a preparative $SiO_2$ TLC plate developed with 8% MeOH/DCM to afford 41 mg of I-9 as a white solid.

EXAMPLE 20

1-[4-tert-Butyl-5-methoxy-2-(2-oxo-1,2-dihydro-pyridin-3-yl)-benzoyl]-piperidine-4-carbonitrite (I-56)

step 1—To a suspension of 4-tert-butyl-3-methoxybenzoic acid (3.00 g, 14.4 mmol, CASRN 79822-46-1) in $H_2O$ (30 mL) was added solid NaOH (1.21 g, 30.2 mmol). NBS (2.81 g, 15.8 mmol) was added in several portions over 10 min. The reaction mixture was stirred at RT for 1 h before additional NaOH (0.12 g, 3.0 mmol) and NBS (0.28 g, 1.6 mmol) were added. After stirring for an additional 1 h, the reaction mixture was acidified with 48% HBr, diluted with $H_2O$ then thrice extracted with $Et_2O$. The combined extracts were washed sequentially with 10% aqueous $Na_2S_2O_3$ and $H_2O$, dried ($MgSO_4$), filtered and concentrated under reduced pressure to afford a pale yellow solid which was dissolved in MeOH (50 mL) and con $H_2SO_4$ (5 mL) was slowly added. The reaction mixture was heated at 70° C. for 3 h, cooled to RT overnight then concentrated under reduced pressure. The residue was diluted with $H_2O$ and thrice extracted with $Et_2O$. The combined extracts were washed with sequentially 1.0 M aq NaOH and $H_2O$, dried ($MgSO_4$), filtered and concentrated under reduced pressure to afford 3.7 g (85%) of 2-bromo-4-tert-butyl-5-methoxybenzoic acid methyl ester (64, CASRN 911115-95-2)

step 2—A microwave vial was charged with 64 (903 mg, 3.00 mmol), 2-benzyloxy-3-(4,4,5,5-tetramethyl-[1,3,2]dioxaborolan-2-yl)pyridine (1.12 g, 3.60 mmol), $Pd(PPh_3)_4$ (173 mg, 0.15 mmol), $Na_2CO_3$ (950 mg, 9.00 mmol), MeOH (10 mL) and DCM (3 mL). The vial was sealed and irradiated at 115° C. for 30 min in microwave synthesizer. The reaction was quenched with $H_2O$ and extracted with DCM. The combined organics were dried ($MgSO_4$) and concentrated under reduced pressure. The residue was purified by $SiO_2$ chromatography eluting with a EtOAc/hexane gradient (10% to 20% EtOAc) to afford 964 mg (80%) of 2-(2-benzyloxypyridin-3-yl)-4-tert-butyl-5-methoxybenzoic acid methyl ester (66) as a light yellow solid.

step 3—To a suspension of 66 (960 mg, 2.36 mmol) in MeOH (15 mL), $H_2O$ (10 mL), and THF (10 mL) was added NaOH (1.00 g, 23.6 mmol). The reaction mixture was heated at 70° C. overnight and gradually became homogeneous. The mixture was cooled to 0° C., acidified to pH 3 with 1.0 M aq HCl and thrice extracted with EtOAc. The combined extracts were dried ($MgSO_4$), filtered and concentrated under reduced pressure to afford 895 mg (97%) of 2-(2-benzyloxypyridin-3-yl)-4-tert-butyl-5-methoxybenzoic acid (68) as a beige solid.

step 4—To a solution of 68 (100 mg, 0.26 mmol) in DMF (3 mL) were added 4 cyano-piperidine (32 mg, 0.29 mmol), HOBt (39 mg, 0.29 mmol), EDCI (56 mg, 0.29 mmol) and DIPEA. The reaction mixture was stirred at RT overnight then quenched with $H_2O$ and thrice extracted with EtOAc. The combined extracts were sequentially washed with $H_2O$ (3 times) and brine, dried ($MgSO_4$), filtered and concentrated under reduced pressure to afford 126 mg (99%) of 1-[2-(2-benzyloxypyridin-3-yl)-4-tert-butyl-5-methoxybenzoyl]piperidine-4-carbonitrile (70) as a pale yellow foam.

step 5—To a solution of 70 (126 mg, 0.26 mmol) in MeOH (8 mL) was added 20% $Pd(OH)_2$/C (20 mg, wet). The reaction mixture was stirred under an atmosphere of hydrogen (balloon) for 2 h then filtered through a CELITE pad and the pad washed with EtOAc. The filtrate was concentrated under reduced pressure to afford 95 mg (93%) of I-56 as an off-white solid: MS=394 $[M+H]^+$.

The following are prepared analogously except in step 4, 4 cyanopiperidine is replaced with the amine in parenthesis: I-40 (morpholine), I-51 (thiomorpholine 1,1-dioxide), I-46 (1-acetyl-piperazine, CASRN 13889-98-0), I-62 (4,4-difluoro-piperidine, CASRN 21987-29-1), I-58 (4-[(methylamino)methyl]-pyridine, CASRN 6971-44-4), I-47 (2-methoxy-N-methyl-ethylamine), I-41 (dimethylamine), I-67 (1-(2-methoxyethyl)-piperazine, CASRN 13484-40-7), I-68 (azetidin-3-ol, CASRN 45347-82-8), I-66 (2-methylaminoacetonitrile, CASRN 5616-32-0), I-73 (3-hydroxymethylpyrrolidine, CASRN 5082-74-6), I-77 (p-fluoro-N-methylbenzyl amine, CASRN 405-66-3), I-79 (4-phenoxypiperidine, CASRN 3202-33-3), I-78 (2-morpholinemethanol, CASRN 103003-01-6), I-85 (aminoacetonitrile, CASRN 540-61-4) and I-80 (ammonium chloride).

EXAMPLE 21

N-[4-tert-Butyl-5-methoxy-2-(6-methyl-2-oxo-1,2-dihydro-pyridin-3-yl)-benzyl]-methanesulfonamide (I-37)

step 1—To a mixture N-(2-bromo-4-tert-butyl-5-methoxybenzyl)-methanesulfonamide (0.25 g, 0.71 mmol), KOAc (0.21 g, 2.14 mmol), bis-(pinacolato)diboron (0.27 g, 1.07 mmol) in DMF (2.5 mL) was added $(dppf)_2Pd(II) Cl_2.2DCM$ (0.02 g, 0.025 mmol). The reaction mixture was stirred at 90° C. for 4 h then cooled to RT, and poured into a satd aq $NH_4Cl$ and extracted with EtOAc. The organic extract was washed sequentially with water and brine, dried ($MgSO_4$), filtered and concentrated. The crude residue was purified by $SiO_2$ chromatography eluting with a EtOAc/hexane gradient (5 to 45% EtOAc) to afford N-[4-tert-butyl-5-methoxy-2-(4,4,5,5-tetramethyl-[1,3,2]dioxaborolan-2-yl)-benzyl]-methanesulfonamide (72).

step 2—A sealed tube containing 72 (51 mg, 0.13 mmol), 2-benzyloxy-3-bromo-6-methyl-pyridine (51 mg, 0.19 mmol), $Na_2CO_3$ (40 mg, 0.38 mmol) and $Pd(PPh_3)_4$ (15 mg, 0.013 mmol) in a mixture of MeOH (3 mL) and DCM (1 mL) was irradiated in a microwave synthesizer at 125° C. for 30 min. The reaction mixture was diluted with DCM, filtered through a pad of CELITE, and the filtrate was concentrated. The crude residue was purified on a preparative $SiO_2$ TLC plate developed with 5% MeOH/DCM to afford 17 mg (28%) of N-[2-(2-benzyloxy-6-methyl-pyridin-3-yl)-4-tert-butyl-5-methoxy-benzyl]-methanesulfonamide (74).

step 3—A mixture of 74 and 10% Pd/C (5 mg) in a mixture of MeOH (8 mL) and EtOAc (4 mL) under 1 atmosphere of $H_2$ at RT was stirred for 1 h. The catalyst was filtered off and the filtrate was concentrated. The crude residue was purified on a preparative SiO$_2$ TLC plate developed with 4% MeOH/DCM to afford 7.3 mg (53%) of I-37.

EXAMPLE 22

N-[4-tert-Butyl-2-(2-oxo-1,2-dihydro-pyridin-3-yl)-phenyl]-methane sulfonamide (I-6) and N-[4-tert-butyl-2-(2-oxo-1,2-dihydro-pyridin-3-yl)-phenyl]-acetamide (I-8)

Suzuki-coupling of N-[2-bromo-4-(1,1-dimethylethyl) phenyl]-acetamide (CASRN 91801-97-7) and 2-methoxy-pyridin-3-yl boronic acid according to step 2 of example 1 and cleavage of the pyridinyl methyl ether according to step 5 of example 1 affords I-8. Sulfonylation of 2-bromo-4-tert-butyl-aniline (CASRN 103273-01-4) affords N-(2-bromo-4-tert-butyl-phenyl)-methanesulfonamide which is converted to I-6 analogously.

EXAMPLE 23

4-tert-Butyl-5-methoxy-2-(2-oxo-1,2-dihydro-pyridin-3-yl)-benzoic acid ethyl ester (I-54)

2-(2-Benzyloxypyridin-3-yl)-4-tert-butyl-5-methoxybenzoic acid (76) can be prepared by the procedure described in example 14 except 2-methoxy-pyridin-3-yl boronic acid is replaced with 2-benzyloxy-pyridin-3-ylboronic acid.

step 1—To a solution of 76 (100 mg, 0.26 mmol) in DMF (3 mL) were added Cs$_2$CO$_3$ (101 mg, 0.31 mmol) and iodoethane (25 µL, 0.31 mmol). The reaction mixture was stirred at RT overnight then quenched with H$_2$O and thrice extracted with EtOAc. The combined organics were washed with H$_2$O (3×), dried (MgSO$_4$), filtered and concentrated under reduced pressure to afford 109 mg (99%) of 2-(2-benzyloxypyridin-3-yl)-4-tert-butyl-5-methoxybenzoic acid ethyl ester (78) as a pale yellow foam.

step 2—To a solution of 78 (109 mg, 0.26 mmol) in MeOH (7 mL) and THF (1 mL) was added 20% Pd(OH)$_2$/C (wet, 20 mg). The reaction mixture was stirred under an atmosphere of hydrogen (balloon) for 2 h then filtered through a pad of CELITE, rinsing with EtOAc. The filtrate was concentrated under reduced pressure to afford 79 mg (93%) of I-54 as an off-white solid: MS=330 [M+H]$^+$.

EXAMPLE 24

3-(5-tert-Butyl-2-methanesulfonylmethyl-4-methoxy-phenyl)-1H-pyridin-2-one (I-15)

step 1—To a solution of 2-bromo-4-tert-butyl-5-methoxy-benzyl chloride (162 mg) in DMF (5 mL) at RT was added NaSMe (117 mg). The reaction mixture was then stirred overnight then diluted with water and extracted with EtOAc. The organic layer was washed with brine, dried (Na$_2$SO$_4$), filtered and concentrated to 145 mg of 1-bromo-5-tert-butyl-4-methoxy-2-methylsulfanylmethyl-benzene (80) as a light yellowish oil.

step 2—A sealed tube containing 80 (50 mg), 2-methoxy-3-pyridine boronic acid (38 mg), Na$_2$CO$_3$ (43 g) and Pd(PPh$_3$)$_4$ (19 mg) in a mixture of MeOH (4 mL) and DCM (1 mL) was irradiated in a microwave synthesizer at 120° C. for 30 min. The organic volatiles were removed under reduced pressure. The residue was partitioned between EtOAc and water. The organic layer was washed with brine, dried (Na$_2$SO$_4$), filtered and concentrated. The crude residue was purified on a preparative SiO$_2$ TLC plate developed with 50% EtOAc/hexane to afford 30 mg of 3-(5-tert-butyl-4-methoxy-2-methylsulfanylmethyl-phenyl)-2-methoxy-pyridine (82).

step 3—A mixture of 82 (30 mg), 48% HBr (50 µL) and HOAc (2 mL) in a sealed tube was heated overnight at 70° C. The reaction mixture was cooled to RT, carefully poured into water and neutralized with K$_2$CO$_3$ then extracted with EtOAc. The organic extract was washed with brine, dried (Na$_2$SO$_4$), filtered and concentrated. The crude residue was purified on a preparative SiO$_2$ TLC developed with 8% MeOH/DCM to afford 6 mg of 3-(5-tert-butyl-4-methoxy-2-methylsulfanylmethyl-phenyl)-1H-pyridin-2-one (84) as a white solid. The title compound can be prepared by oxidation of 84 with MCPBA which afford the sulfone I-15 directly.

EXAMPLE 25

3-[5-tert-Butyl-2-((S)-4-isopropyl-2-oxo-oxazolidin-3-ylmethyl)-4-methoxy-phenyl]-1H-pyridin-2-one (I-76)

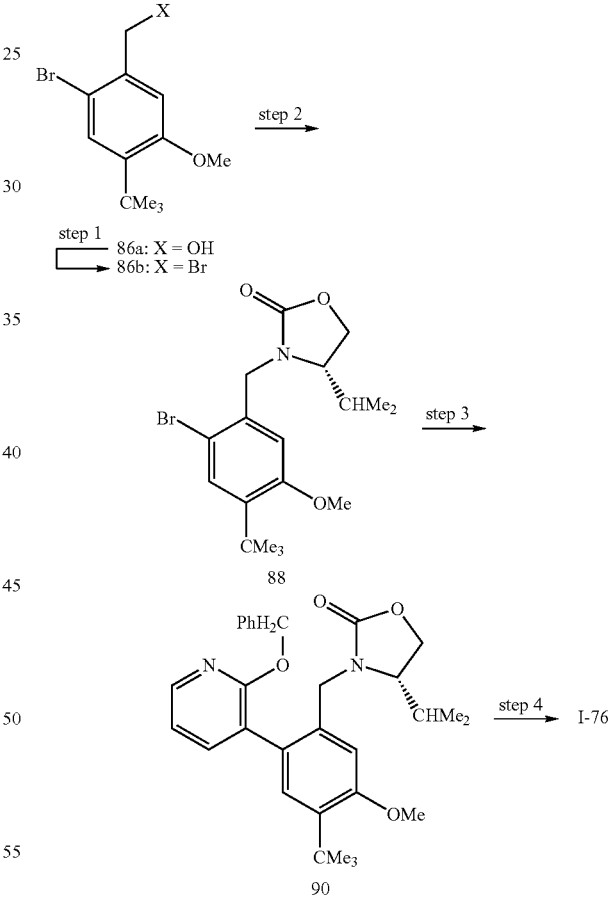

step 1—To a solution of 86a (1 g, 3.6 mmol) and DCM was added PPh$_3$ (1.0 g, 4.0 mmol) then CBr$_4$ (1.3 g, 4.0 mmol) was slowly added (mild exotherm). The reaction mixture was stirred for 20 min then evaporated. The crude product was purified by SiO$_2$ chromatography eluting with a EtOAc/hexane gradient (0 to 25% EtOAc) to afford 1.1 g of 86b.

step 2—To a suspension of NaH (0.250 g, 10.4 mmol) in DMF cooled to 0° C. was added a solution of (S)-4-isopropyl-oxazolidin-2-one (0.770 g, 6.0 mmol) in DMF. After 5 min a solution of 86b (1 g, 2.9 mmol) in DMF was added and the mixture warmed to RT. After 1 h the reaction was quenched with water (20 mL) and extracted four times with EtOAc. The combined extracts were washed with 0.3% aq LiCl (60 mL), dried (MgSO₄), filtered and evaporated. The crude product was purified by SiO₂ chromatography eluting with a EtOAc/hexane gradient (5 to 25% EtOAc) to afford 0.5 g of 88.

Steps 3 and 4 are carried out as described in step 4 of example 10 and in step 4 of example 15 to afford I-76. I-75 was prepared analogously except in step 2, (S)-4-isopropyl-oxazolidin-2-one was replaced with the (R) enantiomer. I-74 is prepared analogously except in step 2, (S)-4-isopropyl-oxazolidin-2-one is replaced with oxazolidin-2-one.

EXAMPLE 26

3-[5-tert-Butyl-4-methoxy-2-(pyridin-2-ylaminomethyl)-phenyl]-1H-pyridin-2-one (I-59)

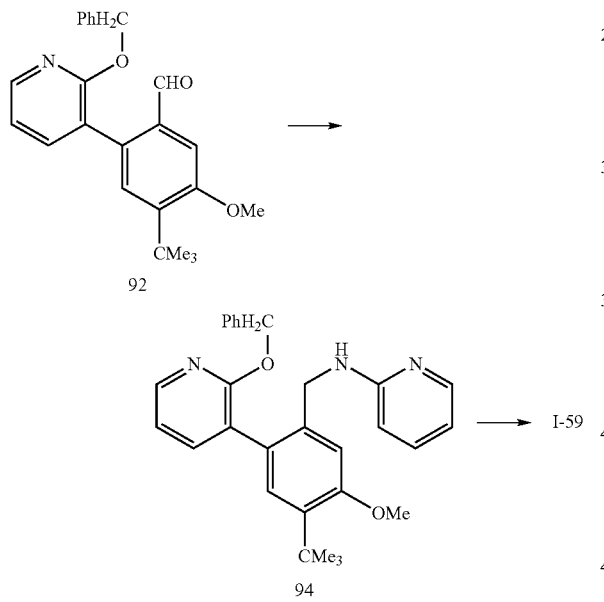

step 1—A mixture of 92 (130 mg, 0.35 mmol, 92 is prepared from 44b by Suzuki-coupling with 2-benzyloxy-pyridin-3-yl boronic acid), 2-aminopyridine (32.6 mg, 0.35 mmol), IPA (1 mL) and HOAc (4 drops) in DCE (10 mL) was stirred overnight at RT. Sodium triacetoxyborohydride (220 mg, 1.05 mmol) was then added and stirring continued overnight at RT. The reaction mixture was carefully poured into a satd aq NaHCO₃ solution then extracted with EtOAc. The organic layer was washed with brine, dried (MgSO₄), filtered and concentrated. The crude residue was purified on a preparative SiO₂ TLC plate developed with 30% EtOAc/hexanes to afford 103 mg (65%) of 94.

step 2—A mixture of 94 (31 mg) and 10% Pd/C (5 mg) in MeOH (15 mL) under 1 atmosphere of H₂ at RT was stirred for 1 h. The catalyst was filtered and the filtrate was concentrated. The crude residue was purified on a preparative SiO₂ TLC plate developed with 10% MeOH/DCM to afford 13 mg (54%) of I-59.

EXAMPLE 27

1-[4-tert-Butyl-5-methoxy-2-(2-oxo-1,2-dihydropyridin-3-yl)-benzyl]-3-methyl-1,3-dihydro-benzoimidazol-2-one (I-69)

step 1—To a solution of 1-methyl-2-benzimidazolinone (260 mg, 1.80 mmol) in DMF (10 mL) was added NaH (72 mg, 1.80 mmol, 60% in mineral oil) and the solution was stirred for 30 min at RT. To this solution was added 26 (500 mg, 1.80 mmol) and the reaction mixture was stirred overnight at 80° C. The reaction was poured into a satd aq NH₄Cl and twice extracted with EtOAc. The combined extracts was washed sequentially with water and brine, dried (MgSO₄), filtered and conce ntrated. The crude residue was purified by SiO₂ chromatography eluting with a EtOAc/hexane gradient (10 to 65% EtOAc) to afford 0.669 g (92%) of 1-(2-bromo-4-tert-butyl-5-methoxy-benzyl)-3-methyl-1,3-dihydro-benzoimidazol-2-one (96).

step 2—A sealed tube containing 96 (100 mg, 0.25 mmol), 2-benzyloxy-pyridin-3-yl boronic acid (85 mg, 0.37 mmol), Na₂CO₃ (80 mg, 0.74 mmol) and Pd(PPh₃)₄ (29 mg, 0.025 mmol) in a mixture of MeOH (1.5 mL) and DCM (0.5 mL) was irradiated on a microwave synthesizer at 100° C. for 30 min. The reaction mixture was diluted with DCM, filtered through a pad of CELITE, and the filtrate was concentrated. The crude residue was purified on a preparative SiO₂ TLC plate developed with 30% EtOAc/hexanes to afford 99 mg of 1-[2-(2-benzyloxy-pyridin-3-yl)-4-tert-butyl-5-methoxy-benzyl]-3-methyl-1,3-dihydro-benzoimidazol-2-one (98).

step 3—A mixture of 98 (99 mg) and 10% Pd/C (15 mg) in MeOH (20 mL) under 1 atmosphere of H₂ at RT was stirred for 2 h. The catalyst was filtered and the filtrate was concentrated. The crude residue was purified on a preparative SiO₂ TLC plate developed with 5% MeOH/DCM to afford 63.7 mg (78%) of I-69.

EXAMPLE 28

(R)-1-[4-tert-Butyl-5-methoxy-2-(2-oxo-1,2-dihydro-pyridin-3-yl)-benzyl]-5-oxo-pyrrolidine-2-carboxylic acid ethyl ester (I-70) and (R)-1-[4-tert-Butyl-5-methoxy-2-(2-oxo-1,2-dihydro-pyridin-3-yl)-benzyl]-5-oxo-pyrrolidine-2-carboxylic acid (I-71)

step 1—To a solution of ethyl (R)-(−)-2-pyrrolidone-5-carboxylate (500 mg, 3.2 mmol) in DMF (15 mL) was added NaH (148 mg, 3.7 mmol, 60% in mineral oil) and the mixture was stirred for 30 min at RT. To the solution was added 26 (900 mg, 3.2 mmol) and the reaction mixture was stirred overnight at 80° C. The reaction mixture was poured into a satd aq NH₄Cl solution then twice extracted with EtOAc. The combined EtOAc extracts were washed sequentially with water and brine, dried (MgSO₄), filtered and concentrated. The crude residue was purified by SiO₂ chromatography eluting with a EtOAc/hexane gradient (10 to 65% EtOAc) to afford 476 mg (36%) of (R)-1-[2-bromo-4-tert-butyl-5-methoxy-benzyl]-5-oxo-pyrrolidine-2-carboxylic acid ethyl ester (100).

step 2—A sealed tube containing 100 (150 mg, 0.36 mmol), 2-benzyloxy-pyridin-3-yl boronic acid (125 mg, 0.56 mmol), Na₂CO₃ (116 mg, 1.1 mmol) and Pd(PPh₃)₄ (42 mg, 0.036 mmol) in a mixture of MeOH (1.5 mL) and DCM (0.5 mL) was irradiated on a microwave synthesizer at 100° C. for 30 min. The reaction mixture was diluted with DCM, filtered through a pad of CELITE, and the filtrate was concentrated. The crude residue was purified on a preparative SiO₂ TLC plate developed with 50% EtOAc/hexanes to afford 140 mg (84%) of (R)-1-[2-(2-benzyloxy-pyridin-3-yl)-4-tert-butyl-5-methoxy-benzyl]-5-oxo-pyrrolidine-2-carboxylic acid ethyl ester (102).

step 3—A mixture of 102 (140 mg) and 10% Pd/C (25 mg) in EtOH (20 mL) under 1 atmosphere of $H_2$ at RT was stirred for 2 h. The catalyst was filtered and the filtrate was concentrated. The crude residue was purified on a preparative $SiO_2$ TLC plate developed with 5% MeOH/DCM to afford 110 mg (96%) of I-70.

A mixture of the I-70 (50 mg, 0.12 mmol), 1N LiOH (0.5 mL), THF (1 mL), MeOH (1 mL) and water (0.5 mL) was stirred overnight at RT. This solution was washed with ether, acidified with 1N HCl and extracted with EtOAc. The organic extract was washed with brine, dried ($MgSO_4$), filtered and concentrated. The crude residue was purified on a preparative $SiO_2$ TLC plate developed with 10% MeOH/DCM containing 0.5% (v/v) formic acid to afford 14.4 mg (30%) of I-71.

EXAMPLE 29

3-[5-tert-Butyl-2-((S)-2-hydroxymethyl-5-oxo-pyrrolidin-1-ylmethyl)-4-methoxy-phenyl]-1H-pyridin-2-one (I-72)

step 1—To a solution of (5S)-5-(tert-butyl-dimethyl-silanyloxymethyl)-2-pyrrolidin-2-one (326 mg, 1.42 mmol, CASRN 106191-02-0) in DMF (15 mL) was added NaH (57 mg, 1.42 mmol, 60% in mineral oil). The mixture was stirred for 30 min at RT then 26 (400 mg, 1.42 mmol) was added and the reaction mixture was stirred overnight at 80° C. The reaction mixture was poured into a satd aq $NH_4Cl$ solution and twice extracted with EtOAc. The combined extracts were washed sequentially with water, and brine, dried ($MgSO_4$), filtered and concentrated. The crude residue was purified by $SiO_2$ chromatography eluting with a EtOAc/hexane gradient (10 to 50% EtOAc) to afford 286 mg (42%) of (S)-1-(2-bromo-4-tert-butyl-5-methoxy-benzyl)-5-(tert-butyl-dimethyl-silanyloxymethyl)-pyrrolidin-2-one (104).

step 2—A sealed tube containing 104 (141 mg, 0.29 mmol), 2-benzyloxy-pyridin-3-yl boronic acid (100 mg, 0.44 mmol), $Na_2CO_3$ (92 mg, 0.87 mmol) and $Pd(PPh_3)_4$ (33 mg, 0.029 mmol) in a mixture of MeOH (1.5 mL) and DCM (0.5 mL) was irradiated in a microwave synthesizer at 100° C. for 30 min. The reaction mixture was diluted with DCM, filtered through a pad of CELITE and the filtrate was concentrated. The crude residue was purified on a preparative $SiO_2$ TLC plate developed with 40% EtOAc/hexanes to afford 128 mg (75%) of (S)-1-[2-(2-benzyloxy-pyridin-3-yl)-4-tert-butyl-5-methoxy-benzyl]-5-(tert-butyl-dimethyl-silanyloxymethyl)-pyrrolidin-2-one (106).

step 3—To a solution of 106 (128 mg, 0.22 mmol) and THF (10 mL) under an argon atmosphere was added dropwise (n-Bu)$_4$N$^+$F$^-$ (0.24 mL, 1M in THF). After 1 h the mixture was poured into 1N HCl, extracted with EtOAc, washed with brine, dried ($MgSO_4$), filtered and concentrated to afford 100 mg (97%) of (S)-1-[2-(2-benzyloxy-pyridin-3-yl)-4-tert-butyl-5-methoxy-benzyl]-5-hydroxymethyl-pyrrolidin-2-one (108).

step 4—A mixture of 108 (100 mg) and 10% Pd/C (15 mg) in MeOH (20 mL) under 1 atmosphere of $H_2$ at RT was stirred for 2 h. The catalyst was filtered off and the filtrate was concentrated. The crude residue was purified on a preparative $SiO_2$ TLC plate developed with 10% MeOH to afford 44.3 mg (55%) of I-72.

I-83 was prepared analogously using (5-R)-5-(tert-butyl-dimethyl-silanyloxymethyl)-2-pyrrolidin-2-one in step 1 in place of the 5-S enantiomer.

EXAMPLE 30

(1S,3S)-3-Methanesulfonylamino-cyclopentanecarboxylic acid 4-tert-butyl-5-methoxy-2-(2-oxo-1,2-dihydro-pyridin-3-yl)-benzylamide (I-81)

step 1—To a mixture of (1S,3S)—N-Boc-1-aminocyclopentane-3-carboxylic acid (300 mg, 1.3 mmol, CASRN 161601-29-2), 19 (360 mg, 1.3 mmol), HOBt (228 mg, 1.7 mmol) in a mixture of THF (2 mL) and DMF (2 mL) cooled to 5° C. was added sequentially TEA (780 mg, 7.8 mmol) and EDCI (160 mg, 1.7 mmol). The mixture was stirred overnight at RT then diluted with EtOAc, washed sequentially with aq 1N HCl, water, brine, dried ($MgSO_4$), filtered and concentrated. The residue was purified by $SiO_2$ chromatography eluting with a EtOAc/hexane gradient (10 to 60% EtOAc) to afford a residue which was further purified on a preparative $SiO_2$ TLC plate developed with 40% EtOAc/hexanes to afford 116 mg (18%) of [(1S,3S)-3-(2-bromo-4-tert-butyl-5-methoxy-benzylcarbamoyl)-cyclopentyl]-carbamic acid tert-butyl ester the amide-bromide (110).

step 2—A sealed tube containing 110 (116 mg, 0.24 mmol), 2-benzyloxy-pyridin-3-yl boronic acid (83 mg, 0.36 mmol), $Na_2CO_3$ (76 mg, 0.72 mmol) and $Pd(PPh_3)_4$ (28 mg, 0.024 mmol) in a mixture of MeOH (6 mL) and DCM (2 mL) was irradiated in a microwave synthesizer at 120° C. for 30 min. The reaction mixture was diluted with DCM, filtered through a pad of CELITE, and the filtrate was concentrated. The crude residue was purified by $SiO_2$ chromatography eluting with a EtOAc/hexane gradient (10 to 65% EtOAc) to afford 102 mg (73%) of {(1S,3S)-3-[2-(2-benzyloxy-pyridin-3-yl)-4-tert-butyl-5-methoxy-benzylcarbamoyl]-cyclopentyl}-carbamic acid tert-butyl ester. This was dissolved in DCM (10 mL) cooled to 5° C. and TFA (0.5 mL) was added dropwise via syringe. The mixture was stirred overnight at RT and concentrated to afford the TFA salt of the free amine. To a solution of the amine-TFA salt (106 mg, 0.18 mmol), TEA (0.15 mL, 1.0 mmol) and DCM (6 mL) cooled to 5° C. and was added dropwise a solution of $MeSO_2Cl$ (0.021 mL, 0.264 mmol) in DCM (2 mL) over a period of 15 min. The reaction was stirred overnight at RT, diluted with EtOAc, washed sequentially with aq 1N HCl and brine, dried ($MgSO_4$.), filtered and evaporated. The crude residue was purified on a preparative $SiO_2$ TLC plate developed with 100% EtOAc to afford 37 mg (37%) of (1S,3S)-3-methanesulfonylamino-cyclopentanecarboxylic acid 2-(2-benzyloxy-pyridin-3-yl)-4-tert-butyl-5-methoxy-benzylamide (112).

step 3—A mixture of 112 (100 mg) and 10% Pd/C (15 mg) in MeOH (20 mL) under 1 atmosphere of $H_2$ at RT was stirred for 2 h. The catalyst was filtered off and the filtrate was concentrated. The crude residue was purified on a preparative $SiO_2$ TLC plate developed with 10% MeOH/DCM to afford 24.5 mg (79%) of I-81.

I-82 was prepared analogously except in step 1, (1S,3S)—N-Boc-1-aminocyclopentane-3-carboxylic acid was replaced with 3-[[(1,1-dimethylethoxy)carbonyl]amino]-cyclohexane-carboxylic acid (CASRN 334932-13-7).

EXAMPLE 31

(2R,4S)-4-Methanesulfonylamino-pyrrolidine-2-carboxylic acid 4-tert-butyl-5-methoxy-2-(2-oxo-1,2-dihydro-pyridin-3-yl)-benzylamide (I-84)

step 1—To a solution of 2R-trans-4-amino-1,2-pyrrolidinedicarboxylic acid, 1-(1,1-dimethylethyl) ester (460 mg, 1.65 mmol, CASRN 132622-78-7) in DCM (4 mL) cooled to 5° C. was added TEA (420 mg, 4 mmol). A solution of MeSO$_2$Cl (0.15 mL, 2 mmol) in DCM (2 mL) was added over a period of 15 min. The mixture was stirred overnight at RT then poured slowly into a solution of aq 1N HCl. The solution was extracted with EtOAc, the extract washed with brine, dried (MgSO$_4$), filtered and concentrated to afford 569 mg (100%) of the sulfonamide. The sulfonamide was stirred in a solution of 1N LiOH (7 mL), THF (7 mL) and MeOH (7 mL) overnight at RT. The solution was acidified and extracted into 10% MeOH/DCM (100 mL), dried (Na$_2$SO$_4$), filtered and concentrated to afford 545 mg (100%) of (2R,4S)-4-methanesulfonylamino-pyrrolidine-1,2-dicarboxylic acid 1-tert-butyl ester (114).

step 2—To a mixture of 114 (545 mg, 1.77 mmol), 19 (530 mg, 1.77 mmol), HOBt (290 mg, 2.12 mmol) in THF (5 mL) and DMF (5 mL) cooled to 5° C. was added sequentially TEA (720 mg, 7.08 mmol) and EDCI (440 mg, 2.3 mmol). The mixture was stirred overnight at RT, diluted with EtOAc, washed sequentially with aq 1N HCl, water and brine, dried (MgSO$_4$), filtered and concentrated. The residue was purified by SiO$_2$ chromatography eluting with a EtOAc/hexane gradient (50 to 100% EtOAc) to provide a residue which was further purified on a preparative SiO$_2$ TLC plate developed with EtOAc to afford 170 mg (17%) of (2R,4S)-4-methane-sulfonylamino-pyrrolidine-2-carboxylic acid 2-bromo-4-tert-butyl-5-methoxy-benzylamide the amide-bromide (116).

The synthesis of I-84 was completed by Suzuki-coupling of 116 and 2-benzyloxy-pyridin-3-yl boronic acid and catalytic hydrogenolysis as described in steps 2 and 4 of example 29. The crude product was purified on a preparative SiO$_2$ TLC plate developed with 10% MeOH/DCM to afford 19 mg of I-84.

EXAMPLE 32

4-tert-Butyl-3-methoxy-6-(2-oxo-1,2-dihydro-pyridin-3-yl)-2-propyl-benzoic acid methyl ester (I-90)

step 1—To a solution of 3-methoxy-4-tert-butylbenzoic acid (1.0 eq, 48.02 mmol, 10.00 g and NaOAc (2.0 eq, 96.03 mmol, 7.88 g) in HOAc (75 mL) at RT was added dropwise Br$_2$ (2.0 eq, 96.03 mmol, 4.94 mL). The resulting mixture was heated at 50° C. for 24 h, cooled to RT and poured into a mixture of ice-water. The slightly orange-colored solid was collected by suction filtration, washed with water, dried in the oven at 40° C. to afford 12.87 g of 6-bromo-4-tert-butyl-3-methoxybenzoic acid the product (118).

step 2—To a solution of 118 (1.0 eq, 5.22 mmol, 1.50 g) in DCM (50 mL) cooled to 0° C. was added dropwise a solution of BBr$_3$ in DCM (3.0 eq, 15.67 mmol, 15.67 mL, 1.0 M solution). The resulting mixture was warmed to RT and stirred for 24 h. The reaction was cooled to 0° C. and quenched with ice-water. The white precipitate was collected by suction filtration, washed with water and dried to afford 1.01 g of 6-bromo-4-tert-butyl-3-hydroxybenzoic acid (120).

step 3—To a solution of 120 (1.0 eq, 2.27 mmol, 621 mg) in DCM (10 mL) at RT was added in three portions NBS (2.0 eq, 4.55, 809 mg). The mixture was stirred RT for 30 min. The reaction was diluted with water, the organic layer was separated, dried (MgSO$_4$) and concentrated to afford 767 mg of 2,6-dibromo-4-tert-butyl-3-hydroxybenzoic acid (122) as a light brownish solid.

step 4—To a solution of 122 (1.0 eq, 2.18 mmol, 767 mg) in acetone (15 mL) was added K$_2$CO$_3$ (3.0 eq, 6.54 mmol, 903 mg) and MeI (5.0 eq, 10.89 mmol, 680 µL). The mixture was heated at 60° C. for 2 h before it was cooled to RT and the organic volatiles were removed under reduced pressure. The residue was partitioned between in EtOAc and water. The organic layer was separated, washed with brine, dried and concentrated. The crude was purified by SiO$_2$ chromatography eluting with a EtOAc/hexane gradient (5 to 30% EtOAc) to afford 278 mg of 2,6-dibromo-4-tert-butyl-3-methoxybenzoic acid (124).

step 5—Methyl 6-(2-benzyloxy-pyridin-3-yl)-2-bromo-4-tert-butyl-3-methoxy-benzoate (126) was prepared by Suzuki coupling of 124 as described in step 2 of example 29 except Pd(dppf)Cl$_2$.CH$_2$Cl$_2$ was used in place of Pd(PPh$_3$)$_4$. The crude product was purified by SiO$_2$ chromatography eluting with a EtOAc/hexane (1 to 15% EtOAc).

step 6—A sealed tube containing a mixture of 126 (1.0 eq, 0.14 mmol, 70 mg), 2-allyl-4,4,5,5-tetramethyl-[1,3,2]dioxaborolane (2.0 eq, 0.29 mmol, 49 mg), Pd(PPh$_3$)$_4$ (0.1 eq, 0.01 mmol, 17 mg) and CsF (2.2 eq, 0.32 mmol, 48 mg) in MeOH (4 mL) and DCM (1 mL), was irradiated in a microwave synthesizer for 30 min at 115° C. The organic solvents were removed and the residue was partitioned between EtOAc and water. The organic layer was separated, dried (MgSO$_4$) and concentrated. The crude was purified by SiO$_2$ chromatography eluting with a EtOAc/hexane gradient (1 to 15% EtOAc) to afford 17 mg of methyl 2-allyl-6-(2-benzyloxy-pyridin-3-yl)-4-tert-butyl-3-methoxy-benzoate (128).

step 7—A mixture of 128 (17 mg) and Pd(OH)$_2$/C (20 mg) in EtOAc (10 mL) was stirred under 1 atm H$_2$ for 30 min then the catalyst was filtered off. The filtrate was concentrated to afford 4.9 mg of I-90 as a waxy solid.

EXAMPLE 33

HCV NS5B RNA Polymerase Activity

The enzymatic activity of HCV polymerase (NS5B570n-Con1) was measured as the incorporation of radiolabeled nucleotide monophosphates into acid insoluble RNA products. Unincorporated radiolabeled substrate was removed by filtration and scintillant was added to the washed and dried filter plate containing radiolabeled RNA product. The amount of RNA product generated by NS5B570-Con1 at the end of the reaction was directly proportional to the amount of light emitted by the scintillant.

The N-terminal 6-histidine tagged HCV polymerase, derived from HCV Con1 strain, genotype 1b (NS5B570n-Con1) contains a 21 amino acid deletion at the C-terminus relative to the full-length HCV polymerase and was purified from E. coli strain BL21(DE) pLysS. The construct, containing the coding sequence of HCV NS5B Con1 (GenBank accession number AJ242654) was inserted into the plasmid construct pET17b, downstream of a T7 promoter expression cassette and transformed into E. coli. A single colony was grown overnight as a starter culture and later used inoculate 10 L of LB media supplemented with 100 µg/mL ampicillin at 37° C. Protein expression was induced by the addition of 0.25 mM isopropyl-β-D-thiogalactopyranoside (IPTG) when optical density at 600 nM of the culture was between 0.6 and 0.8 and cells were harvested after 16 to 18 h at 30° C. NS5B570n-Con1 was purified to homogeneity using a three-step protocol including subsequent column chromatography on Ni-NTA, SP-Sepharose HP and Superdex 75 resins.

Each 50 µl enzymatic reaction contained 20 nM RNA template derived from the complementary sequence of the Internal Ribosome Entry Site (cIRES), 20 nM NS5B570n-Con1 enzyme, 0.5 µCi of tritiated UTP (Perkin Elmer catalog no. TRK-412; specific activity: 30 to 60 Ci/mmol; stock solution concentration from 7.5×10-5 M to 20.6×10-6 M), 1 µM each ATP, CTP, and GTP, 40 mM Tris-HCl pH 8.0, 40 mM NaCl, 4 mM DTT (dithiothreitol), 4 mM MgCl2, and 5 µl of compound serial diluted in DMSO. Reaction mixtures were assembled in 96-well filter plates (cat #MADVN0B, Millipore Co.) and incubated for 2 h at 30° C. Reactions were stopped by addition of 10% final (v/v) trichloroacetic acid and incubated for 40 min at 4° C. Reactions were filtered, washed with 8 reaction volumes of 10% (v/v) trichloroacetic acetic acid, 4 reaction volumes of 70% (v/v) ethanol, air dried, and 25 µl of scintillant (Microscint 20, Perkin-Elmer) was added to each reaction well.

The amount of light emitted from the scintillant was converted to counts per minute (CPM) on a Topcount® plate reader (Perkin-Elmer, Energy Range: Low, Efficiency Mode: Normal, Count Time: 1 min, Background Subtract: none, Cross talk reduction: Off).

Data was analyzed in Excel® (Microsoft®) and ActivityBase® (Idbs®). The reaction in the absence of enzyme was used to determine the background signal, which was subtracted from the enzymatic reactions. Positive control reactions were performed in the absence of compound, from which the background corrected activity was set as 100% polymerase activity. All data was expressed as a percentage of the positive control. The compound concentration at which the enzyme-catalyzed rate of RNA synthesis was reduced by 50% ($IC_{50}$) was calculated by fitting $$Y = \% \text{ Min} + \frac{(\% \text{ Max} - \% \text{ Min})}{\left[1 + \frac{X}{(IC_{50})^S}\right]} \quad (i)$$

equation (i) to the data. where "Y" corresponds to the relative enzyme activity (in %), "% Min" is the residual relative activity at saturating compound concentration, "% Max" is the relative maximum enzymatic activity, "X" corresponds to the compound concentration, and "S" is the Hill coefficient (or slope).

EXAMPLE 34

HCV Replicon Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla luciferase* gene was introduced into the first open reading frame of a genotype 1b replicon construct NK5.1 (N. Krieger et al., *J. Virol.* 2001 75(10):4614), immediately after the internal ribosome entry site (IRES) sequence, and fused with the neomycin phosphotransferase (NPTII) gene via a self-cleavage peptide 2A from foot and mouth disease virus (M. D. Ryan & J. Drew, *EMBO* 1994 13(4):928-933). After in vitro transcription the RNA was electroporated into human hepatoma Huh7 cells, and G418-resistant colonies were isolated and expanded. Stably selected cell line 2209-23 contains replicative HCV subgenomic RNA, and the activity of *Renilla luciferase* expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express *Renilla luciferase* reporter, were cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using the *R. luciferase* Assay system (Promega cat no. E2820). All the reagents described in the following paragraph were included in the manufacturer's kit, and the manufacturer's instructions were followed for preparations of the reagents. The cells were washed once with 100 ml of phosphate buffered saline (pH 7.0) (PBS) per well and lysed with 20 ml of 1×*R. luciferase* Assay lysis buffer prior to incubation at room temperature for 20 min. The plate was then inserted into the Centro LB 960 microplate luminometer (Berthold Technologies), and 100 µl of *R. luciferase* Assay buffer was injected into each well and the signal measured using a 2-second delay, 2-second measurement program. $IC_{50}$, the concentration of the drug required for reducing replicon level by 50% in relation to the untreated cell control value, can be calculated from the plot of percentage reduction of the luciferase activity vs. drug concentration as described above.

WST-1 reagent from Roche Diagnostic (cat no. 1644807) was used for the cytotoxicity assay. Ten microliter of WST-1 reagent was added to each well of the transparent plates including wells that contain media alone as blanks. Cells were then incubated for 2 h at 37° C., and the OD value was measured using the MRX Revelation microtiter plate reader (Lab System) at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration as described above.

TABLE II

| Compound Number | HCV Replicon Activity IC50 (µM) | Cytotoxic Activity CC50 (µM) |
|---|---|---|
| I-63 | 0.034 | 43.7 |
| I-34 | 0.936 | 44.2 |
| I-21 | 0.168 | — |
| I-38 | 0.31 | 92.9 |
| I-81 | 0.238 | — |

EXAMPLE 35

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound according to formula I wherein:

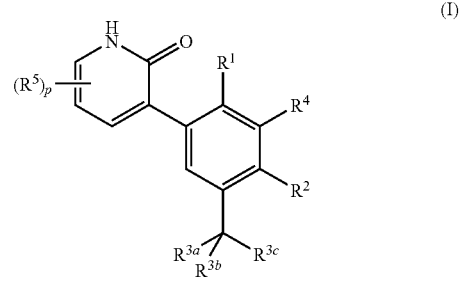

(I)

$R^1$ is (alkylene)$_{0-6}$COX, (alkylene)$_{0-6}$NR$^a$R$^b$, (alkylene)$_{0-6}$CN, $C_{1-6}$ hydroxyalkyl, or $C_{1-3}$ alkylsulfonyl-(alkylene)$_{0-3}$;

X is hydrogen, hydroxy, $C_{1-6}$ alkoxy or NR$^c$R$^d$;

$R^2$ is hydrogen, $C_{1-6}$ alkoxy, $C_{1-3}$ alkyl or halogen;

$R^a$ is (a) hydrogen, (b) $C_{1-6}$ alkyl, (c) $C_{1-6}$ acyl, (d) aroyl, (e) —SO$_2$—$C_{1-6}$ alkyl, (f) —SO$_2$-aryl, (g) —SO$_2$—$C_{1-3}$ arylalkyl, (h) aryl-$C_{1-3}$ alkyl, or (i) SO$_2$NR$^e$R$^f$ wherein R$^e$ and R$^f$ are independently hydrogen or $C_{1-3}$ alkyl, (j) pyridinoyl, (k) $C_{3-7}$ cycloalkyl-carbonyl or (l) CONHR$^e$R$^f$, (m) —SO$_2$—$C_{3-6}$ cycloalkyl or (n) 4-methanesulfonylamino-pyrrolidine-2-carbonyl wherein said cycloalkane moiety is substituted by $C_{1-3}$ alkylsulfonylamino and wherein said aryl, said aroyl and said pyridinoyl are each independently optionally substituted with one to three groups independently selected from hydroxy, $C_{1-6}$ alkoxy, $C_{1-6}$ alkoxy, amino, $C_{1-3}$ alkylamino, $C_{1-3}$ dialkylamino, $C_{1-6}$ acylamino, $C_{1-6}$ alkylsulfonylamino, bis-($C_{1-6}$ alkylsulfonyl)amino, $C_{1-6}$ alkyl and halogen;

$R^b$ is hydrogen $C_{1-6}$ alkyl, optionally substituted aryl, $C_{1-6}$ hydroxyalkyl, $C_{1-3}$ acyloxy-$C_{1-6}$ alkyl, heterocyclyl-$C_{1-3}$ alkyl; $C_{3-6}$ cycloalkyl-$C_{1-3}$ alkyl, pyrrolidin-3-ylmethyl, 1-acetyl-pyrrolidin-3-ylmethyl, piperidin-4-yl, or pyridinyl; or, $R^a$ and $R^b$ together are C(=O)C(Me)$_2$NHC(=O), (CH$_2$)$_{3-5}$S(=O)$_2$, (CH$_2$)$_{2-5}$C(=O), C(=O)CH$_2$C(Me)$_2$CH$_2$C(=O), HC=CC(Br)=CHC(=O), C(=O)(CH$_2$)$_{2-4}$C(=O), HC=CC(=O)CEt$_2$(=O) or S(=O)$_2$NR$^6$(CH$_2$)$_{3-5}$ wherein R$^6$ is hydrogen, $C_{1-6}$ alkyl or Boc; or, $R^a$ and $R^b$ together with the nitrogen to which they are attached are (a) phthaloyl (b) 1-methyl-1,3-dihydro-2-oxo-benzoimidazol-3-yl, (c) 5-oxo-pyrrolidin-1-yl optionally substituted by $C_{1-6}$ carboalkoxy, carboxyl or $C_{1-3}$ hydroxymethyl, (d) 3-hydroxymethyl-pyrrolidin-1-yl, (e) 2-oxo-oxazolidin-3-yl optionally substituted with $C_{1-6}$ alkyl or (f) 3-oxo-2,3-dihydro-1H-isoindolyl optionally substituted with $C_{1-6}$ alkylsulfonylamino or $C_{3-6}$ cycloalkylsulfonylamino;

$R^c$ is hydrogen, $C_{1-6}$ alkyl;

$R^d$ is hydrogen, $C_{1-6}$ alkyl; pyridinyl-$C_{1-3}$ alkyl, cyano-$C_{1-3}$ alkyl, $C_{1-3}$ alkoxy-$C_{1-6}$ alkyl or aryl-$C_{1-3}$ alkyl optionally substituted with halogen; or, $R^c$ and $R^d$ together are $(CH_2)_2X^1(CH_2)_2$ wherein $X^1$ is O, $SO_2$ or $NR^7$ wherein $R^7$ is hydrogen, $C_{1-6}$ alkyl, $C_{1-3}$ alkoxy-$C_{1-3}$ alkyl or $C_{1-3}$ acyl, or, $R^c$ and $R^d$ together with the nitrogen to which they are attached are 4,4-difluoro-piperidin-1-yl, 4-phenoxy-piperidin-1-yl, 3-hydroxy-azetidine, 4-cyano-piperidin-1-yl, 3-(hydroxylmethyl)pyrrolidin-1-yl or 2-hydroxymethyl-morpholin-4-yl;

$R^{3a}$, $R^{3b}$ and $R^{3c}$ (i) when taken independently are selected independently from $C_{1-3}$ alkyl, $C_{1-2}$ alkoxy or $C_{1-2}$ fluoroalkyl or (ii) when taken together, $R^{3a}$ and $R^{3b}$ together are $C_{2-4}$ methylene and $R^{3c}$ is $C_{1-3}$ alkyl;

$R^4$ is hydrogen, $C_{1-6}$ alkyl;

$R^5$ is hydrogen, halogen or $C_{1-3}$ alkyl;

p is zero to three; or, a pharmaceutically acceptable salt thereof.

2. A compound according to claim 1 wherein $R^2$ is hydrogen or $C_{1-6}$ alkoxy and $R^{3a}$, $R^{3b}$ and $R^{3c}$ are methyl.

3. A compound according to claim 1 wherein $R^1$ is (alkylene)$_{0-6}NR^aR^b$, $R^a$ is optionally substituted aroyl, $C_{3-7}$ cycloalkanecarbonyl, —$SO_2C_{1-6}$ alkyl, —$SO_2$—$C_{3-6}$ cycloalkyl, $SO_2NR^eR^f$, pyridinoyl, $R^b$ is hydrogen, $C_{1-6}$ alkyl, aryl or pyridinyl.

4. A compound according to claim 3 where $R^1$ is (alkylene)$_{0-3}NR^aR^b$, $R^2$ is hydrogen or $C_{1-6}$ alkoxy and $R^{3a}$, $R^{3b}$ and $R^{3c}$ are methyl.

5. A compound according to claim 1 wherein $R^1$ is (alkylene)$_{0-6}NR^aR^b$ and $R^a$ and $R^b$ together are $S(=O)_2NR^6(CH_2)_p$ wherein p is 3 to 5.

6. A compound according to claim 5 where $R^1$ is (alkylene)$_{0-3}NR^aR^b$, $R^2$ is hydrogen or $C_{1-6}$ alkoxy and $R^{3a}$, $R^{3b}$ and $R^{3c}$ are methyl.

7. A compound according to claim 1 wherein $R^1$ is (alkylene)$_{0-6}NR^aR^b$ and $R^a$ and $R^b$ together with the nitrogen to which they are attached are (a) phthaloyl, (b) 1-methyl-1,3-dihydro-2-oxo-benzoimidazol-3-yl, (c) 5-oxo-pyrrolidin-1-yl optionally substituted $C_{1-6}$ carboalkoxy, carboxy $C_{1-3}$ hydroxymethyl, (d) 3-hydroxymethyl-pyrrolidin-1-yl (e) 2-oxo-oxazolidin-3-yl optionally substituted with $C_{1-6}$ alkyl or (f) 3-oxo-2,3-dihydro-1H-isoindolyl optionally substituted with $C_{1-6}$ alkylsulfonylamino or $C_{3-6}$ cycloalkylsulfonylamino.

8. A compound according to claim 1 wherein $R^1$ is (alkylene)$_{0-6}$COX, X is $C_{1-6}$ alkoxy or $NR^cR^d$.

9. A compound according to claim 8 wherein $R^1$ is (alkylene)$_{0-3}$COX, $R^2$ is hydrogen or $C_{1-6}$ alkoxy and $R^{3a}$, $R^{3b}$ and $R^{3c}$ are methyl.

10. A compound according to claim 1 selected from the group consisting of:

3-[4-tert-Butyl-5-methoxy-2-(2-oxo-1,2-dihydro-pyridin-3-yl)-phenyl]-propionic acid;

3-(5-tert-Butyl-2-hydroxymethyl-4-methoxy-phenyl)-1H-pyridin-2-one;

3-[4-tert-Butyl-5-methoxy-2-(2-oxo-1,2-dihydro-pyridin-3-yl)-phenyl]-propionic acid methyl ester;

4-tert-Butyl-5-methoxy-2-(2-oxo-1,2-dihydro-pyridin-3-yl)-benzoic acid;

3-[5-tert-Butyl-2-(2-hydroxy-ethyl)-4-methoxy-phenyl]-1H-pyridin-2-one;

N-[4-tert-Butyl-2-(2-oxo-1,2-dihydro-pyridin-3-yl)-phenyl]-methanesulfonamide;

[4-tert-Butyl-5-methoxy-2-(2-oxo-1,2-dihydro-pyridin-3-yl)-phenyl]-acetic acid;

N-[4-tert-Butyl-2-(2-oxo-1,2-dihydro-pyridin-3-yl)-phenyl]-acetamide;

4-tert-Butyl-5-methoxy-N-methyl-2-(2-oxo-1,2-dihydro-pyridin-3-yl)-benzamide;

2-[4-tert-Butyl-5-methoxy-2-(2-oxo-1,2-dihydro-pyridin-3-yl)-phenyl]-N-methyl-acetamide;

2-[4-tert-Butyl-5-methoxy-2-(2-oxo-1,2-dihydro-pyridin-3-yl)-phenyl]-acetamide;

N-[4-tert-Butyl-5-methoxy-2-(2-oxo-1,2-dihydro-pyridin-3-yl)-benzyl]-acetamide;

N-[4-tert-Butyl-5-methoxy-2-(2-oxo-1,2-dihydro-pyridin-3-yl)-benzyl]-methanesulfonamide;

N-[4-tert-Butyl-5-methoxy-2-(2-oxo-1,2-dihydro-pyridin-3-yl)-benzyl]-N-methyl-acetamide;

3-(5-tert-Butyl-2-methanesulfonylmethyl-4-methoxy-phenyl)-1H-pyridin-2-one;

3-[5-tert-Butyl-2-(1,1-dioxo-1$\lambda^6$-[1,2]thiazinan-2-ylmethyl)-4-methoxy-phenyl]-1H-pyridin-2-one;

N-{2-[4-tert-Butyl-5-methoxy-2-(2-oxo-1,2-dihydro-pyridin-3-yl)-phenyl]-ethyl}-methanesulfonamide;

3-[5-tert-Butyl-4-methoxy-2-(2-oxo-pyrrolidin-1-ylmethyl)-phenyl]-1H-pyridin-2-one;

N-[4-tert-Butyl-5-methoxy-2-(2-oxo-1,2-dihydro-pyridin-3-yl)-benzyl]-4-chloro-benzenesulfonamide;

N-[4-tert-Butyl-5-methoxy-2-(2-oxo-1,2-dihydro-pyridin-3-yl)-benzyl]-C-phenyl-methanesulfonamide;

3-[5-tert-Butyl-2-(1,1-dioxo-1$\lambda^6$-isothiazolidin-2-ylmethyl)-4-methoxy-phenyl]-1H-pyridin-2-one;

N-[4-tert-Butyl-5-methoxy-2-(2-oxo-1,2-dihydro-pyridin-3-yl)-benzyl]-N-methyl-benzamide;

3-[5-tert-Butyl-4-methoxy-2-(2-oxo-piperidin-1-ylmethyl)-phenyl]-1H-pyridin-2-one;

Ethanesulfonic acid 4-tert-butyl-5-methoxy-2-(2-oxo-1,2-dihydro-pyridin-3-yl)-benzylamide;

Propane-2-sulfonic acid 4-tert-butyl-5-methoxy-2-(2-oxo-1,2-dihydro-pyridin-3-yl)-benzylamide;

N-Benzyl-N-[4-tert-butyl-5-methoxy-2-(2-oxo-1,2-dihydro-pyridin-3-yl)-benzyl]-methanesulfonamide;

N-[4-tert-Butyl-5-methoxy-2-(2-oxo-1,2-dihydro-pyridin-3-yl)-benzyl]-N-ethyl-methanesulfonamide;

N-[4-tert-Butyl-5-methoxy-2-(2-oxo-1,2-dihydro-pyridin-3-yl)-benzyl]-N-isopropyl-methanesulfonamide;

1-[4-tert-Butyl-5-methoxy-2-(2-oxo-1,2-dihydro-pyridin-3-yl)-benzyl]-pyrrolidine-2,5-dione;

Acetic acid 2-{[4-tert-butyl-5-methoxy-2-(2-oxo-1,2-dihydro-pyridin-3-yl)-benzyl]-methanesulfonyl-amino}-ethyl ester;

N-[4-tert-Butyl-5-methoxy-2-(2-oxo-1,2-dihydro-pyridin-3-yl)-benzyl]-N-pyrrolidin-3-ylmethyl-methanesulfonamide;

N-Butyl-N-[4-tert-butyl-5-methoxy-2-(2-oxo-1,2-dihydro-pyridin-3-yl)-benzyl]-methanesulfonamide;

2-[4-tert-Butyl-5-methoxy-2-(2-oxo-1,2-dihydro-pyridin-3-yl)-benzyl]-isoindole-1,3-dione;

N-[4-tert-Butyl-5-methoxy-2-(2-oxo-1,2-dihydro-pyridin-3-yl)-benzyl]-N-phenyl-methanesulfonamide;

N-[4-tert-Butyl-5-methoxy-2-(2-oxo-1,2-dihydro-pyridin-3-yl)-benzyl]-N-(2-hydroxy-ethyl)-methanesulfonamide;

N-[4-tert-Butyl-5-methoxy-2-(2-oxo-1,2-dihydro-pyridin-3-yl)-benzyl]-benzamide;

N-[4-tert-Butyl-5-methoxy-2-(6-methyl-2-oxo-1,2-dihydro-pyridin-3-yl)-benzyl]-methanesulfonamide;

N-[4-tert-Butyl-5-methoxy-2-(2-oxo-1,2-dihydro-pyridin-3-yl)-benzyl]-4-hydroxy-benzamide;

1-[4-tert-Butyl-5-methoxy-2-(2-oxo-1,2-dihydro-pyridin-3-yl)-benzyl]-3,3-diethyl-1H-pyridine-2,4-dione;
3-[5-tert-Butyl-4-methoxy-2-(morpholine-4-carbonyl)-phenyl]-1H-pyridin-2-one;
4-tert-Butyl-5-methoxy-N,N-dimethyl-2-(2-oxo-1,2-dihydro-pyridin-3-yl)-benzamide;
4-Amino-N-[4-tert-butyl-5-methoxy-2-(2-oxo-1,2-dihydro-pyridin-3-yl)-benzyl]-benzamide;
N-[4-tert-Butyl-5-methoxy-2-(2-oxo-1,2-dihydro-pyridin-3-yl)-benzyl]-4-methanesulfonylamino-benzamide;
N-[4-tert-Butyl-5-methoxy-2-(2-oxo-1,2-dihydro-pyridin-3-yl)-benzyl]-4-bis-(methanesulfonyl)amino-benzamide
N-[4-tert-Butyl-2-(5-fluoro-2-oxo-1,2-dihydro-pyridin-3-yl)-5-methoxy-benzyl]-methanesulfonamide;
3-[2-(4-Acetyl-piperazine-1-carbonyl)-5-tert-butyl-4-methoxy-phenyl]-1H-pyridin-2-one;
4-tert-Butyl-5-methoxy-N-(2-methoxy-ethyl)-N-methyl-2-(2-oxo-1,2-dihydro-pyridin-3-yl)-benzamide;
N-(1-Acetyl-pyrrolidin-3-ylmethyl)-N-[4-tert-butyl-5-methoxy-2-(2-oxo-1,2-dihydro-pyridin-3-yl)-benzyl]-methanesulfonamide;
N-[4-tert-Butyl-5-methoxy-2-(2-oxo-1,2-dihydro-pyridin-3-yl)-benzyl]-nicotinamide;
N-[4-tert-Butyl-5-methoxy-2-(2-oxo-1,2-dihydro-pyridin-3-yl)-benzyl]-sulfamide
3-[5-tert-Butyl-2-(1,1-dioxo-1$\lambda^6$-thiomorpholine-4-carbonyl)-4-methoxy-phenyl]-1H-pyridin-2-one;
N-{1-[4-tert-Butyl-5-methoxy-2-(2-oxo-1,2-dihydro-pyridin-3-yl)-phenyl]-ethyl}-methanesulfonamide;
N-{1-[4-tert-Butyl-5-methoxy-2-(2-oxo-1,2-dihydro-pyridin-3-yl)-phenyl]-ethyl}-N-methyl-methanesulfonamide;
4-tert-Butyl-5-methoxy-2-(2-oxo-1,2-dihydro-pyridin-3-yl)-benzoic acid ethyl ester;
Propane-2-sulfonic acid [4-tert-butyl-5-methoxy-2-(2-oxo-1,2-dihydro-pyridin-3-yl)-benzyl]-cyclobutylmethyl-amide;
1-[4-tert-Butyl-5-methoxy-2-(2-oxo-1,2-dihydro-pyridin-3-yl)-benzoyl]-piperidine-4-carbonitrile;
N-[4-tert-Butyl-5-methoxy-2-(2-oxo-1,2-dihydro-pyridin-3-yl)-benzyl]-N-piperidin-4-yl-methanesulfonamide;
4-tert-Butyl-5-methoxy-N-methyl-2-(2-oxo-1,2-dihydro-pyridin-3-yl)-N-pyridin-4-ylmethyl-benzamide;
3-[5-tert-Butyl-4-methoxy-2-(pyridin-2-ylaminomethyl)-phenyl]-1H-pyridin-2-one;
3-[5-tert-Butyl-2-(1,1-dioxo-1$\lambda^6$-[1,2,5]thiadiazolidin-2-ylmethyl)-4-methoxy-phenyl]-1H-pyridin-2-one;
5-[4-tert-Butyl-5-methoxy-2-(2-oxo-1,2-dihydro-pyridin-3-yl)-benzyl]-1,1-dioxo-1$\lambda^6$-[1,2,5]thiadiazolidine-2-carboxylic acid tert-butyl ester;
3-[5-tert-Butyl-2-(4,4-difluoro-piperidine-1-carbonyl)-4-methoxy-phenyl]-1H-pyridin-2-one;
N-[4-tert-Butyl-5-methoxy-2-(2-oxo-1,2-dihydro-pyridin-3-yl)-benzyl]-3-methanesulfonylamino-benzamide;
3-[5-tert-Butyl-4-methoxy-2-(5-methyl-1,1-dioxo-1$\lambda^6$-[1,2,5]thiadiazolidin-2-ylmethyl)-phenyl]-1H-pyridin-2-one;
N-[4-tert-Butyl-5-methoxy-2-(2-oxo-1,2-dihydro-pyridin-3-yl)-benzyl]-3-methanesulfonylamino-N-methyl-benzamide;
4-tert-Butyl-N-cyanomethyl-5-methoxy-N-methyl-2-(2-oxo-1,2-dihydro-pyridin-3-yl)-benzamide;
3-{5-tert-Butyl-4-methoxy-2-[4-(2-methoxy-ethyl)-piperazine-1-carbonyl]-phenyl}-1H-pyridin-2-one;
3-[5-tert-Butyl-2-(3-hydroxy-azetidine-1-carbonyl)-4-methoxy-phenyl]-1H-pyridin-2-one;
1-[4-tert-Butyl-5-methoxy-2-(2-oxo-1,2-dihydro-pyridin-3-yl)-benzyl]-3-methyl-1,3-dihydro-benzoimidazol-2-one;
(R)-1-[4-tert-Butyl-5-methoxy-2-(2-oxo-1,2-dihydro-pyridin-3-yl)-benzyl]-5-oxo-pyrrolidine-2-carboxylic acid ethyl ester;
(R)-1-[4-tert-Butyl-5-methoxy-2-(2-oxo-1,2-dihydro-pyridin-3-yl)-benzyl]-5-oxo-pyrrolidine-2-carboxylic acid;
3-[5-tert-Butyl-2-((S)-2-hydroxymethyl-5-oxo-pyrrolidin-1-ylmethyl)-4-methoxy-phenyl]-1H-pyridin-2-one;
3-[5-tert-Butyl-2-(3-hydroxymethyl-pyrrolidine-1-carbonyl)-4-methoxy-phenyl]-1H-pyridin-2-one;
3-[5-tert-Butyl-4-methoxy-2-(2-oxo-oxazolidin-3-ylmethyl)-phenyl]-1H-pyridin-2-one;
3-[5-tert-Butyl-2-((R)-4-isopropyl-2-oxo-oxazolidin-3-ylmethyl)-4-methoxy-phenyl]-1H-pyridin-2-one;
3-[5-tert-Butyl-2-((S)-4-isopropyl-2-oxo-oxazolidin-3-ylmethyl)-4-methoxy-phenyl]-1H-pyridin-2-one;
4-tert-Butyl-N-(4-fluoro-benzyl)-5-methoxy-N-methyl-2-(2-oxo-1,2-dihydro-pyridin-3-yl)-benzamide;
3-[5-tert-Butyl-2-(2-hydroxymethyl-morpholine-4-carbonyl)-4-methoxy-phenyl]-1H-pyridin-2-one;
3-[5-tert-Butyl-4-methoxy-2-(4-phenoxy-piperidine-1-carbonyl)-phenyl]-1H-pyridin-2-one;
4-tert-Butyl-5-methoxy-2-(2-oxo-1,2-dihydro-pyridin-3-yl)-benzamide;
(1S,3S)-3-Methanesulfonylamino-cyclopentanecarboxylic acid 4-tert-butyl-5-methoxy-2-(2-oxo-1,2-dihydro-pyridin-3-yl)-benzylamide;
3-Methanesulfonylamino-cyclohexanecarboxylic acid 4-tert-butyl-5-methoxy-2-(2-oxo-1,2-dihydro-pyridin-3-yl)-benzylamide;
3-[5-tert-Butyl-2-((R)-2-hydroxymethyl-5-oxo-pyrrolidin-1-ylmethyl)-4-methoxy-phenyl]-1H-pyridin-2-one;
(1S,4S)-4-Methanesulfonylamino-pyrrolidine-2-carboxylic acid 4-tert-butyl-5-methoxy-2-(2-oxo-1,2-dihydro-pyridin-3-yl)-benzylamide;
4-tert-Butyl-N-cyanomethyl-5-methoxy-2-(2-oxo-1,2-dihydro-pyridin-3-yl)-benzamide;
N-[4-tert-Butyl-5-methoxy-2-(2-oxo-1,2-dihydro-pyridin-3-yl)-benzyl]-N-methyl-methanesulfonamide;
N-[4-tert-Butyl-5-methoxy-2-(2-oxo-1,2-dihydro-pyridin-3-yl)-benzyl]-2-chloro-benzenesulfonamide;
1-[4-tert-Butyl-5-methoxy-2-(2-oxo-1,2-dihydro-pyridin-3-yl)-benzyl]-4,4-dimethyl-piperidine-2,6-dione;
N-[4-tert-Butyl-5-methoxy-2-(2-oxo-1,2-dihydro-pyridin-3-yl)-benzyl]-N-phenyl-acetamide;
4-tert-Butyl-3-methoxy-6-(2-oxo-1,2-dihydro-pyridin-3-yl)-2-propyl-benzoic acid methyl ester; and,
N-{2-[4-tert-Butyl-5-methoxy-2-(2-oxo-1,2-dihydro-pyridin-3-yl)-benzyl]-3-oxo-2,3-dihydro-1H-isoindol-5-yl}-methanesulfonamide; or
a pharmaceutically acceptable salt thereof.

11. A pharmaceutical composition comprising a therapeutically effective quantity of a compound according to claim 1 admixed with at least one pharmaceutically acceptable carrier, diluent or excipient.

* * * * *